United States Patent [19]

Innami et al.

[11] Patent Number: 5,428,000
[45] Date of Patent: Jun. 27, 1995

[54] ANTAGONISM INHIBITORS FOR HERBICIDES, HERBICIDE COMPOSITIONS AND HERBICIDAL METHODS

[75] Inventors: Haruki Innami, Utsunomiya; Teruyuki Misumi, Yokohama; Makoto Konnai, Utsunomiya, all of Japan

[73] Assignee: Toho Chemical Industry Co., Ltd., Tokyo, Japan

[21] Appl. No.: 216,777

[22] Filed: Mar. 23, 1994

Related U.S. Application Data

[63] Continuation-in-part of Ser. No. 76,402, Jun. 14, 1993, abandoned.

[30] Foreign Application Priority Data

Jun. 26, 1992 [JP] Japan .................... 4-191317

[51] Int. Cl.$^6$ ........................... A01N 25/32
[52] U.S. Cl. ..................... 504/104; 424/78.36
[58] Field of Search ............... 504/105, 104; 424/78.36

[56] References Cited

PUBLICATIONS

"The Basis of Bentazon Antagonism on Sethoxydin . . . " Wanamarta et al. Weed Sci. (1989) 37, 400–404.
"Herbicide Antagonism at the Whole Plant Level", Green, Weed Technology (1989) 3, 217–226.
"Effect of Bentazon, Imazaquin, and Chlorimuron on . . . ", Groon et al, Weed Sci. (1989) 37, 645–650.
The Effects of Anti-Antagonistics Adjuvant A–1 and FA–2 on Herbicidal Antagonism, Washington, Jul. 4–9, 1994.
Effects of Surface Active Agents in Mixed Application with a Herbicide for *Gramineae* Weeds and Bentazone, Japan Weed Society Apr. 2–3, 1992.
Effects of Surface Active Agents in Mixed Applications with a Herbicide for *Gramineae* Weeds and a Herbicide for Broadleaf Weeds (II), Japan Weed Society, apr. 6–7 1993.
Effects of Surface Active Agents in Mixed Applications with a Herbicide for *Gramineae* Weeds and a Herbicide for Broadleaf Weeds (II), Japan Weed Society, Apr. 16–17, 1994.
Quizalofop and Setnoxyalm Activity as Affected by Adjuvants and Ammonium Fertilizers, Beckett, et al Weed Science (1992) 40, 12–19.
Foliar Absorption and Phytotoxicity of Quizalofop with lipid Compounds, Manthey, et al, Weed Science (1992) 40, 558–562.
Ammonium sulfate increases efficacy of sethoxydim through increased absorption and translocation, Smith, et al; Weed Science (1992) 40, 351–358.
Antagonism of haloxyfop activity in tall fescue by diacamba and bentazon, Aguero, et al Weed Science (1991) 39, 1–5.
Effects of methylammonium and urea ammonium nitrate on foliar uptake of thifensulfuron in velvetleaf, Thomas H. Beckett, et al Weed Science (1991) 39, 333–338.
Antagonistic effect of MCPA on fenoxaprop activity, Raymond J. A. Deschamps, et al Weed Science (1990) 38, 62–66.
A basis for the antagonistic effect of 2,4–D on haloxy-methyl toxicity of Johnsongrass, Mueller, et al Weed Science 38, 103–107 (1990).
Interaction of acifluorfen with fluazifop for annual grass control, John L. Godley, et al Weed Science 34, (1986) 936–941.
Johnsongrass control in soybean with postemergence grass herbicides applied alone and in mixtures, Ted Whitwell, et al Weed Science (1985) 33, 673–678.

(List continued on next page.)

Primary Examiner—Allen J. Robinson
Assistant Examiner—Brian G. Bembenick
Attorney, Agent, or Firm—Henry T. Burke

[57] ABSTRACT

An antagonism caused by the use of a herbicide for narrowleaf weeds together with a herbicide for broadleaf weeds is inhibited by using together with hydrophilic polymeric compound containing a quaternary ammonium salt and having 10,000 to 1,000,000 of molcular weight.

6 Claims, No Drawings

PUBLICATIONS

The effect of adjuvants and oil carriers on photodecomposition of 2,4-D, bentazon, and haloxyfop, Harrison, et al Weed Science (1985) 34, 81-87.

Influence of application variables on antagonism between sethoxydim and bentazon, Rhodes, et al Weed Sci. (1984) 32, 436-441.

Compatibility of BAS 9052 OH with acifluorfen and bentazon, Robert G. Hartzler, et al Weed Science (1984) 31, 597-599.

Sethoxydim and broadleaf herbicide interaction effects on annual grass control in peanuts, W. James Grichar Weed Techno. (1991) 5, 321-324.

Differential effects of UAN on antagonism with bentazon, B. Clifford Gerwick, et al Weed Technology (1991) 5, 620-624.

Herbicide antagonism at the whole plant level, Jerome M. Green Weed Technology (1989) 3, 217-226.

Postemergence grass and broadleaf herbicide interactions for red rice control in soybeans, Minton, et al Weed Techn. (1989) 3, 329-334.

Effect of bentazon, imazaquin, and chlorimuron on the absorption and translocation of the methyl ester of haloxyfop, Croon, et al Weed Sci. (1989) 37, 645-650.

Influence of 2,4-D and MCPA formulations and oil on diclofop phytotoxicity, Greg F. Gillespie, et al Weed Sci. (1989) 37, 380-384.

The basis of bentazon antagonism on sethoxydim absorption and activity, Gunawan Wanamarta, et al Weed Sci. (1989) 37, 400-404.

Barnyardgrass control with grass and broadleaf weed herbicide combinations, Minton, et al Weed Sci. (1989) 37, 223-227.

Influence of thiameturon and DPX-L5300 on wild oats control with Barban, Diclofop, AC 222293, and difenzoquat, Charlotte V. Egerlein, et al Weed Sci. 91988) 36, 792-799.

Potential mechanisms for bentazon antagonism with haloxyfop B. Clifford Gerwick III Weed Sci. (1988) 36, 286-290.

Proso millet control in corn with postemergence directed herbicides, James A. Fawcett, et al Weed Science (1988) 36 215-220.

Effect of chlorsulfuron on the movement and fate of diclofop in Italian ryegrass and wheat, Rex Liebl, et al Weed Sci. (1987) 35, 623-628.

The interaction of acifluorfen and bentazon in herbicidal combinations, Weed Sci. (1987) 35, 449-456.

Carrier volume effects on the antagonism of sethoxydim by bentazon, Ralph B. Lassiter, et al Weed Sci (1987) 35, 541-546.

Effect of chlorsulfuron on diclofop phytotoxicity to Italian ryegrass, Rex Liebl, et al Weed Sci (1987) 35, 383-387.

Interaction of acifluorfen with fluazifop for annual grass control, John L. Godley, et al Weed Sci. (1986) 34, 936-941.

ANTAGONISM INHIBITORS FOR HERBICIDES, HERBICIDE COMPOSITIONS AND HERBICIDAL METHODS

RELATED APPLICATION

This is a continuation-in-part of U.S. Ser. No. 08/076,402 filed Jun. 14, 1993.

BACKGROUND OF THE INVENTION

The present invention relates to antagonism inhibitors for herbicides which inhibit antagonism between herbicides for narrowleaf weeds and herbicides for broadleaf weeds when these herbicides are used in combination, herbicide compositions containing the antagonism inhibitor, the herbicides for narrowleaf weeds and the herbicides for broadleaf weeds, and a herbicidal method using these three agents.

From the labor-saving point of view, it is preferred to apply simultaneously herbicides for narrowleaf weeds and herbicides for broadleaf weeds in order to kill simultaneously narrowleaf weeds and broadleaf weeds which grow in the natural world, for example, farming land such as a plowland or a paddy field and non-farming land such as garden, railway bed or river bed. However, it is well known that when these are simultaneously used, there is brought about the so-called antagonism that herbicidal action or weeding action (hereinafter sometimes referred to as "herbicidal action") of one or both of these herbicides is reduced due to their interaction. It is also well known that the reduction in herbicidal action on narrowleaf weeds due to the use of the herbicides for broadleaf weeds together with those for narrowleaf weeds is conspicuous in antagonism caused by the use of both the herbicides in combination.

As one countermeasure for solving the problem, employed is a method of applying the herbicide for narrowleaf weeds and the herbicide for broadleaf weeds each alone at least twice at an interval of several days to kill the narrowleaf weeds and broadleaf weeds separately.

As another countermeasure, employed is a method of applying a mixture of these herbicides at one time wherein the application amount of the herbicide, especially the herbicide for narrowleaf weeds which compensates for the herbicidal action reduced due to the antagonism is increased.

However, the former method suffers from the problem that since the herbicides are applied at least twice, labors and amounts of adjuvants such as spreader and carriers such as water must be increased depending on increase in the number of application.

On the other hand, in the latter method, one application suffices, but amount of the herbicide, especially the herbicide for narrowleaf weeds must be increased to compensate for the herbicidal action reduced due to the antagonism. The possibility of causing the chemical injury for useful crops increases due to the increase of the application amount.

Accordingly, if chemicals which can inhibit the antagonism brought about when herbicides for narrowleaf weeds and those of broadleaf weeds are used in combination are developed, the various defects in the above-mentioned conventional application methods can be removed, weeding can be efficiently performed with less labor, without increasing the amounts of adjuvants, carriers and herbicides and with causing less chemical injure and besides, since amount of the herbicides need not be increased, the possibility of adversely affecting the environment can be reduced.

The inventors have conducted intensive research in an attempt to develop chemicals which can inhibit the antagonism brought about when herbicides for narrowleaf weeds and those of broadleaf weeds are used in combination. As a result, it has been found that this antagonism can be inhibited by using a specific hydrophilic polymeric compound containing a quaternary ammonium salt selected from many compounds. Thus, the present invention has been accomplished.

SUMMARY OF THE INVENTION

That is, the present invention relates to an antagonism inhibitor for herbicides which comprises a hydrophilic polymeric compound containing a quaternary ammonium salt and which inhibits the antagonism brought about when herbicides for narrowleaf weeds and those for broadleaf weeds are used in combination. The present invention further relates to a herbicide composition which comprises a herbicide for narrowleaf weeds and that for broadleaf weeds and said antagonism inhibitor for herbicides which comprises a hydrophilic polymeric compound containing a quaternary ammonium salt and to a herbicidal method of using these three agents.

The herbicides for narrowleaf weeds referred to above are preferably those which are nonionic and effective for foliage applications. The herbicides for broadleaf weeds referred to above are preferably those which are anionic and effective for foliage applications.

The hydrophilic polymeric compound containing a quaternary ammonium salt which is an active ingredient in the antagonism inhibitor for herbicides of the present invention (hereinafter sometimes referred to as "quaternary ammonium salt-containing polymeric compound") has a number-average molecular weight of 10,000 to 1,000,000 and is constituted of a monomer containing a quaternary ammonium salt group and a monomer containing no quaternary ammonium salt group, the ratio of the monomer containing a quaternary ammonium salt group and the monomer containing no quaternary ammonium salt group being 5:95 to 100:0.

The number-average molecular weight of the quaternary ammonium salt-containing polymeric compounds is measured by an aqueous gel permeation chromatography using polyethylene glycol as a standard substance.

The number-average molecular weight of the quaternary ammonium salt-containing polymeric compounds varies depending on the kinds, properties and concentration of bases (compound which is an effective substance) of the respective herbicides for narrowleaf weeds and those for broadleaf weeds and the adjuvants and can be optionally selected from the above range.

The quaternary ammonium salt-containing polymeric compounds must be hydrophilic and the larger hydrophilicity is preferred. The hydrophilicity of the quaternary ammonium salt-containing polymeric compounds is expressed by the distribution coefficient (log POW) measured by a method using water/octanol.

The hydrophilicity of the quaternary ammonium salt-containing polymeric compounds in the present invention in practical use is usually $-2$ or larger, preferably $-2$ to $+2$, especially preferably $-1.7$ to $+1.5$ as the distribution coefficient.

The hydrophilic quaternary ammonium salt-containing polymeric compounds naturally also include so-called water-soluble quaternary ammonium salt-containing polymeric compounds.

The quaternary ammonium salt-containing hyrdophilic polymeric compounds are preferably those which are represented by any of the following formulas (1) and (2):

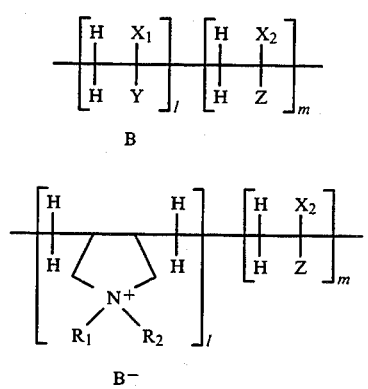

wherein B represents a group having an annion, or a halogen atom, specifically, $Cl^-$, $Br^-$, $CH_3SO_3^-$, $C_2H_5SO_4^-$, $NO_3^-$ or $(CH_3)_2PO_4^-$, among which $Cl^-$ is preferred; each of $X_1$ and $X_2$ represents a hydrogen atom or methyl group, most preferably, X, being a hydrogen atom; each of $R_1$ and $R_2$ represents a methyl, ethyl or propyl group with the total carbon number of $R_1+R_2$ of 2 to 6, in which the total carbon number of $R_1+R_2$ of 2 (each methyl group) is preferred; and the ratio of $l:m$ is 5:95 to 100:0, preferably, 30:70 to 70:30. Molecular weight of the hydrophilic polymeric compounds is 10,000 to 1,000,000.

In the above formula (1), Y represents a unit having a quaternary ammonium salt, specifically, a unit as shown below:

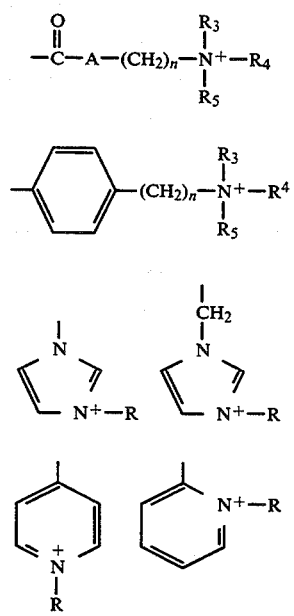

wherein A represents an oxygen atom or —NH—; n is 0 to 4, preferably, n=2 or n=3; each of $R_3$, $R_4$, $R_5$ and R represents a methyl, ethyl or propyl group, and the total carbon number of $R_3+R_4+R_5$ is 3 to 9, in which the total carbon number of $R_3+R_4+R_5$ of 3 (each methyl group) is preferred.

In the above formulas, Z represents a unit having no quaternary ammonium salt, specifically, a unit as shown below;

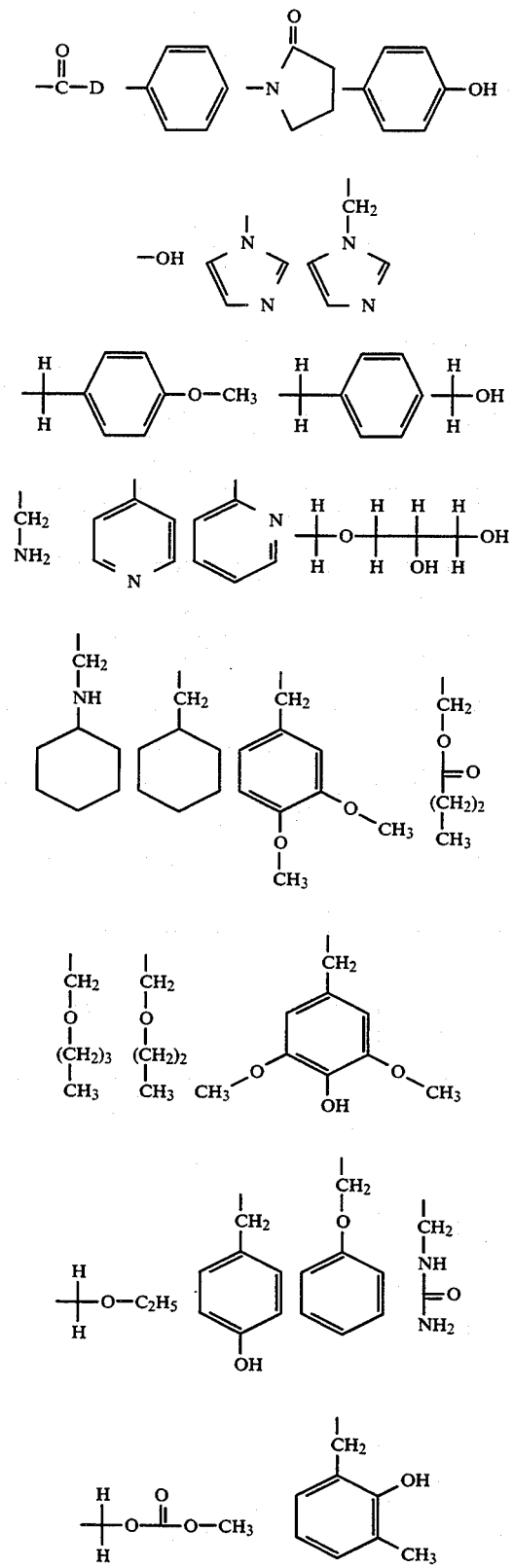

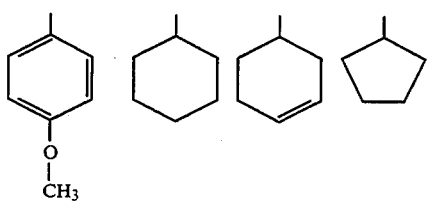

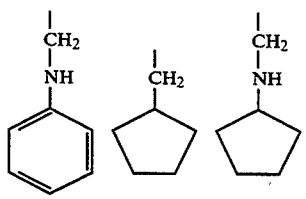

wherein D is a group from —OH, —NH₂, —NHCH₂NH₂, —NHCH₂CH₂NH₂, —NHCH₂CH₂CH₂NH₂, —OCH₂NH₂, —OCH₂CH₂NH₂, —OCH₂CH₂CH₂NH₂, —N(CH₃)₂, —NHCH₂N(CH₃)₂, —NHCH₂CH₂N(CH₈)₂, —NHCH₂CH₂CH₂N(CH₃)₂, —OCH₂N(CH₃)₂, —OCH₂CH₂N(CH₃)₂ and —OCH₂CH₂CH₂N(CH₃)₂, in which —NH₂ is particularly preferred.

Thus, the preferable units for Z include

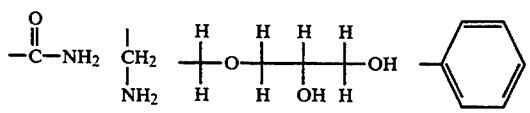

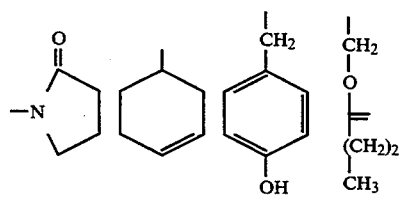

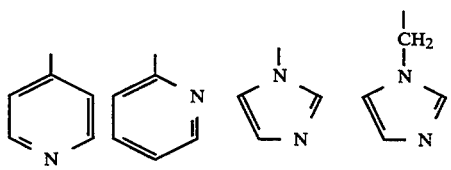

more preferably,

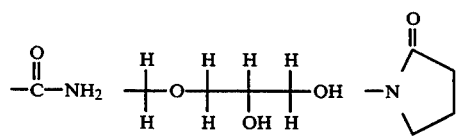

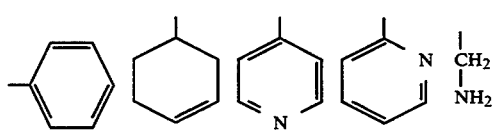

most preferably,

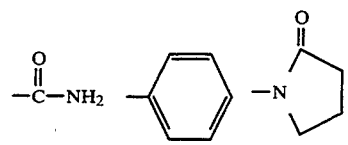

The monomer containing quaternary ammonium salt group and the monomer containing no quaternary ammonium salt group which constitute the quaternary ammonium salt-containing polymeric compound can be optionally selected, for example, in correspondence to the desired quaternary ammonium salt-containing polymeric compound represented by the above formula.

Typical examples of the monomer containing quaternary ammonium salt contain 1,1-dimethyl-3,4-dimethylenepirrolidinium, trimethylaminoethyl acrylate, trimethylaminoethyl methacrylate, acryloyloxypropyltrimethylammonium, methacryloyloxypropyltrimethylammonium, vinylbenzyltrimethylammonium. 3-methyl-1-vinylimidazoliuim, 3-methyl-1-allylimidazolium, 1-methyl-4-vinylpyridinium and 1-methyl-2-vinylpyridinium, as a cationic ion; and fluorine, chlorine and bromine ions, and methyl sulfate, ethyl sulfate, nitrate and dimethyl phosphate radicals, as an anionic ion, in which chlorine ion is a preferred anionic ion.

Typical examples of the monomer containing no quaternary ammonium salt include acrylic acid and methacrylic acid and their acid derivatives, styrene, vinylpyrrolidone, vinyl alcohol, vinylimidazole, allylimidazole, allylamine, allyl alcohol, vinylpyridine, allyloxy-1,2-propanediol, allylphenol, allylphenol ether, allyl propyl ether, allylurea, vinylanisole, vinylcyclohexane, 4-vinyl-1-cyclohexene, vinylcyclopentene, 4-allyl-1,2-dimethoxybenzene, 4-allyl-2,6-dimethoxylphenol, allyl ethyl ether, allyl methyl carbonate, 2-allyl-6-methylphenol, N-allylaniline, allylanisole, allylbenzene, allyl butyl ether, allyl butyrate. allylcyclohexylamine, allylcyclopentene, allylcyclopentylamine and vinylphenol, among which acrylic acid amide, styrene and vinylpyrrolidone are preferred.

If the ratio l:m is outside the range of 5:95 to 100:0, the antagonism inhibiting action decreases. There is a possibility to make the quaternary ammonium salt-containing polymeric compound unsuitable for practical use as an antagonism inhibitor for herbicides.

The amount of the quaternary ammonium salt-containing polymeric compound used as the antagonism inhibitor for herbicides of the present invention varies depending on the varieties of the herbicides and weeds, but is generally 0.001 to 5% by weight, preferably 0.005 to 0.5% by weight on the basis of the application solution which is a dilute prepared by diluting the herbicides for narrowleaf weeds or broadleaf weeds with water or the like.

When the antagonism inhibitor is used in the amount as above on the basis of both the herbicides, the dosage of the antagonism inhibitor of the present invention is generally about 0.05 to 1500 g, preferably about 0.1 to 500 g per 10a although it depends on the dilution ratio of the herbicides.

The antagonism inhibitor for herbicides of the present invention is previously mixed with herbicides for narrowleaf weeds and those for broadleaf weeds and optionally, adjuvants such as surface active agents and spreaders and the mixture is formulated into a preparation and is used as a concentrate like ordinary herbicides.

The formulations in this case include usual formulations for herbicides, such as emulsifiable concentrates, flowable formulation, wettable powders, granules, dusts, granular wettable powders (WDG), liquids, EW agents and microemulsions.

Many of these formulations are normally diluted with water in use.

As the adjuvants, there may be suitably used anionic surface active agents, cationic surface active agents, nonionic surface active agents and amphoteric surface active agents, fatty acids and derivatives thereof, animal oils, vegetable oils and mineral oils, and liquid fertilizers. Practically more preferred are nonionic surface active agents, amphoteric surface active agents, fatty acids and derivatives thereof, mineral oils and liquid fertilizers.

As aforementioned, the adjuvant is previously mixed with the antagonism inhibitor of the present invention, the herbicide for narrowleaf weeds and the herbicide for broadleaf weeds and the mixture can be used as a concentrate formulated like the ordinary herbicides. In addition, the adjuvant can be mixed just before application of herbicides and the antagonism inhibitor without previously adding to the formulation. Furthermore, the adjuvant can be separately applied at the time of the application of herbicides and the antagonism inhibitor without previous addition thereof.

The inhibiting action against antagonism caused by use of herbicides for narrowleaf weeds and broadleaf weeds in combination can be further improved by using the above-mentioned adjuvants together with the antagonism inhibitors of the present invention.

Amount of the adjuvant used with the antagonism inhibitor is in the range of 0.01 to 5% by weight, preferably 0.5 to 3% by weight based on the amount of the application solution.

The anionic surface active agents, cationic surface active agents, nonionic surface active agents and amphoteric surface active agents used in the present invention are preferably water-soluble. These surface active agents can be used each alone or in combination of two or more.

The anionic surface active agents used as adjuvants in the present invention are preferably those which contain hydrophilic groups represented by the formulas —COOQ, —OSO$_3$Q, —SO$_3$Q, —OPO$_3$Q$_2$ and (—O)$_2$-PO$_2$Q (wherein Q represents sodium, potassium, ammonium, monoethanolamine, diethanolamine or triethanolamine).

Examples of the cationic surface active agents used as adjuvants in the present invention are primary fatty amines, secondary fatty amines and tertiary fatty amines, quaternary ammonium salts, trialkylbenzylammonium salts, alkylpyridinium salts, 2-alkyl-1-alkyl-1-hydroxyethylimidazolinium salts, N,N-dialkylmorpholinium salts, polyethylenepolyamino fatty acid amide salts, salts of urea condensates of polyethylenepolyamino fatty acid amides and quaternary ammonium salts of urea condensates of polyethylenepolyamino fatty acid amides. Furthermore, as atoms or groups which constitute the salts, mention may be made of chlorine, bromine, CH$_3$COO—, C$_2$H$_5$COO— and C$_3$H$_7$COO— and chlorine is most preferred.

The nonionic surface active agents used as adjuvants in the present invention are, for example, those which are prepared using, as hydrophilic starting materials, ethylene oxide, polyethylene glycol, glycerin, pentaerythritol, sorbitol, sorbitan, sugar and sucrose. Examples of the noionic surface active agents are polyoxyethylenealkyl ether, polyoxyethylenealkylphenyl ether, polyoxyethylenepolystyrylphenyl ether, Polyoxyethylene-polyoxypropylene glycol, polyoxyethylene-polyoxypropylene alkyl ether, partial esters of polyhydric alcohols and fatty acids, partial esters of polyoxyethylene polyhydric alcohols and fatty acids, poloxyethylene fatty acid esters, polyglycerin fatty acid esters, polyoxyethylenated castor oil and fatty acid diethanolamides. They have a hydrophilicity, namely, an HLB of generally about 3 to 20, preferably about 7 to 15.

Examples of the present polymeric compounds are shown in the Tables 1—1, 1-2, 1-3, 1-4 and 1-5, set forth later.

Typical examples of the surface active agents are polyoxyethylene glycol, polyoxyethylenepolyoxypropylene glycol, polyoxyethylene-2-butylhexyl ether, Polyoxyethylenedodecyl ether, polyoxyethylenetridecyl ether, polyoxyethyleneoleyl ether, polyoxyethyleneoctylphenyl ether, polyoxyethylenenonylphenyl ether, polyethylene glycol palmitate, polyethylene glycol oleate, polyethylene glycol resinate, betaine lauryldimethylaminoacetate, 2-alkyl-N-carboxymethyl-N-hydroxyethylimidazolinium betaine, undecyl-N-hydroxyethyl-N-carboxymethylimidazolinium betaine, N-dodecylbetaine and lauric amidepropylbetaine.

The fatty acids and derivatives thereof used as adjuvants in the present invention are compounds represented by the formula R$_6$COOR$_7$ ( where R$_6$ represents a hydrocarbon group of 6 to 28, preferably 12 to 18 carbon atoms and R$_7$ represents a hydrogen atom or a hydrocarbon group of 1 to 12 carbon atoms, preferably a hydrogen atom or a hydrocarbon group of 1 to 8 carbon atoms). R$_6$ and R$_7$ may be either saturated or unsaturated and may have a side chain or may be straight or cyclic. The derivatives are preferably esters.

Examples of the fatty acids and derivatives thereof used as adjuvants in the present invention are lauric acid, myristic acid, palmitic acid, stearic acid and oleic acid, and methyl laurate, methyl myristate, methyl palmirate, methyl stearate, methyl oleate, methyl linoleate, ethyl laurate, ethyl myristate, ethyl palmirate, ethyl stearate, ethyl oleate, 2-ethylhexyl laurate, 2-ethylhexyl myristate, 2-ethylhexyl palmitate, 2-ethylhexyl stearate, 2-ethylhexyl oleate, octyl laurate, octyl myristate, octyl palmirate, octyl stearate and octyl oleate.

The animal oils used as the adjuvants include, for example, chrysalis oil and beef tallow oil and hardened oils thereof prepared by hydrogenation.

The vegetable oils used as the adjuvants include, for example, linseed oil, sunflower oil, castor oil, cotton seed oil, coconut oil, peanut oil, soybean oil, olive oil, rape oil and resin oil and furthermore, hardened oils thereof prepared by hydrogenation.

The mineral oils used as the adjuvants include, for example, hydrocarbon compositions containing paraffinic hydrocarbons, olefinic hydrocarbons, alicyclic hydrocarbons and/or aromatic hydrocarbons and obtained by distillation of petroleum. Typical examples thereof are light oil, kerosene, spindle oil, machine oil, motor oil and cylinder oil, The liquid fertilizers used as the adjuvants are those which are prepared by dissolving in water the nitrogen components, phosphoric acid components, potassium components and the like customarily used as fertilizer components.

The nitrogen component fertilizers may be any of ammonia nitrogen, nitrate nitrogen and urea nitrogen and typical examples are ammonium sulfate, ammonium nitrate, ammonium phosphate and urea.

The phosphoric acid components may be either water-soluble or citric-soluble and examples are phosphates such as potassium phosphate and ammonium phosphate.

Examples of the potassium components are potassium salts such as potassium sulfate and potassium chloride.

The herbicides for narrowleaf weeds and those for broadleaf weeds used in combination with the antagonism inhibitors of the present invention may be any of those which are customarily used and cause antagonism when used in combination with each other.

However, the herbicides for narrowleaf weeds mentioned above are preferably those which are nonionic and effective for foliage applications, and the herbicides for broadleaf weeds mentioned above are preferably those which are anionic and effective for foliage applications.

When the useful crops are soybean, typical examples of herbicides for narrowleaf weeds are sethoxydim, alloxidim, fluazifop-butyl, quizalofopethyl and fenoxaprop-ethyl. Typical examples of the herbicides for broadleaf weeds which cause antagonism when used in combination with the herbicides for narrowleaf weeds are bentazon, imazaquin, acifluorfensodium, chlorimuron-ethyl, fomesafen, imazethapyr, thifensulfuronmethyl and 2,4-PA.

The ratio of the herbicide for narrowleaf weeds and that for broadleaf weeds can be optionally selected depending on the kinds of these herbicides, the kinds of crops, the kinds, the amount and the distribution of weeds. Generally, the ratio of the applying amount of the herbicide for broadleaf weeds to that for narrowleaf weeds is within the range of 50:1 to 1:5,000, preferably 10:1 to 1:1,000.

The mechanism according to which the effectiveness of the present antagonism inhibitors is expressed is not yet clear, but it is presumed as follows:
(A) There are polyanions having —COOH functional group on the surface layer of botanical bodies.
(B) The antagonism inhibitors of the present invention are polycations having quaternary ammonium salt group (B-1), and also are polymeric compounds (B-2).
(C) Accordingly, when an antagonism inhibitor of the present invention is sprayed onto the surface of a botanical body, the polycations of the antagonism inhibitor are combined to the polyanions on the surface of the botanical body to form polyelectrolyte complex in network structure.
(D) The herbicide for narrowleaf weeds sprayed with the present antagonism inhibitor is electrically neutral, and easily absorbed in the botanical body through the adhered layer without suffering the effect of electric charge at the adhered layer.
(E) On the other hand, the herbicide for broadleaf weeds sprayed combinedly with the present antagonism inhibitor and the herbicide for narrowleaf weeds is anion having carboxylic acid, carboxylate salt, and/or acidic protons, so that the absorption to the botanical body is deterred because of the repulsion of electric charge at the network structure on the adhered layer and the sieve effect.

Due to the factors as mentioned above, transition to a botanical body of the herbicide for narrowleaf weeds is accelerated, while that of the herbicide for broadleaf weeds is delayed. According to such a time-difference effect, the antogonism inhibitor for herbicides, which is a water-soluble polymeric compound containing quaternary ammonium compound, decreases antagonism occurred when a herbicide for narrowleaf weeds and a herbicide for broadleaf weeds are mixed and applied simultaneously, whereby the herbicidal effect of the herbicide for narrowleaf weeds to narrowleaf weeds is secured.

The herbicide composition of the present invention suffices to be in the form of a mixture of the herbicide for narrowleaf weeds, the herbicide for broadleaf weeds and the antagonism inhibitor at the time of application at the latest. This includes use of the composition as a previously formulated concentrate of the mixture and besides, a mixture prepared by mixing, immediately before application, the antagonism inhibitor, the respective herbicides and adjuvants or mixing mixtures containing either one of these agents and the adjuvants with other agents, especially so-called a mixture prepared by mixing in the garden and further includes dilutions of these mixtures. In addition, it includes application of these three agents separately.

The antagonism inhibitor of the present invention exhibits its inhibiting action for antagonism between the herbicide for narrowleaf weeds and herbicide for broadleaf weeds when it is present in the place where the two herbicides coexist. That is, the antagonism inhibitor of the present invention is applied when the two herbicides are simultaneously applied and besides, it can be applied when one of the two herbicides is applied and after awhile another herbicides is applied while the former herbicide still remains and thus, the two herbicides coexist.

As aforementioned, the herbicide composition of the present invention can optionally contain adjuvants such as spreaders together with the herbicides for narrowleaf and broadleaf weeds and the antagonism inhibitor. As the adjuvants there may be used any of customarily used ones as far as they do not damage the effects of the respective agents and functions of the formulations. However, since one of the components constituting the quaternary ammonium salt-containing polymer compound which is an active ingredient of the antagonism inhibitor of the present invention is a monomer containing a quaternary ammonium salt group, full care must be taken on ionic species of the adjuvants in selecting them.

The weeds to which the herbicide composition of the present invention is applied are unlimited and the weeds in crop lands such as plowland and paddy field and non-crop lands such as railway bed, river bed and garden can be controlled or killed. Examples of the narrowleaf weeds which can be controlled are barnyardgrass, green foxtail, crabgrass, goosegrass, Bermudagrass, Brachiaria plantaginea, quackgrass, johnsongrass, millet, Pennisetum alopecuroides (L.) SPRENG, wild oat, canarygrass, meadow foxtail, Echinochloa oryzicola VASING, Echinochloa crus-galli (L.) BEAUV. var. candata, Echinochloa crus-galli (L.) BEAUV. var. formosensis OHWI. The composition of the present invention is especially effective for control of barnyardgrass, green foxtail, crabgrass, goosegrass, Bermudagrass, Brachiaria plantaginea, quackgrass, johnsongrass, millet, and Pennisetum alopecuroides (L.) SPRENG.

Examples of the broadleaf weeds which can be controlled are Catystegia arvensis L., velvetleaf, sicklepod, common lambsquarters, cocklebur, common purslane, amaranthus, prikly sida, tall morningglory, Frolida purslane, Bidens pilosa L., Raphanus sativus, jimsonweed, dayflower, sun spurge, chickweed, Spergula arvensis, Canada thistle, scarlet pimpernel, wild radish, wild mustard, Shepherds purse, Matricaria chamomilla L., spiny amaranth, black nightshade, Alisma canaliculatum A. BR. et BOUCHE, Anmannia multiflora ROXB, Bidens tripartia L., water starwort, Dopatrium junceum ROXB) HAMILT, Eclipta prostrata (L.) L., Elatine triandra SCHK. var. pedicellata KRYLOV, Lindernia pyxidaria L., Ludwigia prostrata ROXB., Marsilea quadrifolia L., Monochoria vaginalis (BURM. f.) PRESL var. plantaginea (ROXB.) SOLMS-LAUB., drop wort, marshpepper smartweed, Rotala indica (WILLD.) KOEHNE var. uliginosa (MIQ) KOEHNE, Sagittaria aginashi MAKINO, Sagittaria pygmaea MIQ., Sagittaria trifolia L., Vandellia angustifolia BENTH., Cyperus rotundus L., Scirpus juncoides ROXB., Potamogeton distinctus A. BENN., Cyperus serotinus ROTTB., Cyperus difformis L., and Eleocharis kuroguwai OHWI.

The composition of the present invention is especially effective for control of Calystegia arvensis L., velvetleaf, sicklepod, common lambsquarters, cocklebur, common purslane, amaranthus, prikly sida, tall morningglory, Florida pursulane, Bidens pilosa L., Raphanus sativa, jimsonweed, dayflower and sun spurge.

Examples of crops are barley, wheat, rice plants, maize, soybean and cotton plants. Among them, application to soybean-growing land is especially effective.

Time and method of application may be the same as application of usual herbicides. For example, they can be applied to soil or directly to plants. The latter is preferred.

The present invention is illustrated by the following nonlimiting examples.

The quaternary ammonium salt-containing polymeric compounds which are antagonism inhibitors used in the examples are shown in Tables 1—1, 1-2, 1-3, 1-4 and 1-5.

TABLE 1-1

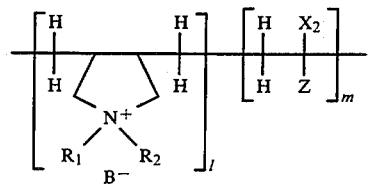

| No. | R₁ | R₂ | Z | X2 | B⁻ | l:m | MW |
|---|---|---|---|---|---|---|---|
| P-1 | CH₃ | CH₃ | $-C(=O)-NH_2$ | H | Cl⁻ | 50:50 | 500,000 |
| P-2 | CH₃ | CH₃ | $-C(=O)-NH_2$ | H | Cl⁻ | 70:30 | 500,000 |
| P-3 | CH₃ | CH₃ | $-C(=O)-NH_2$ | H | Cl⁻ | 30:70 | 500,000 |
| P-4 | CH₃ | CH₃ | $-C(=O)-NH_2$ | H | Cl⁻ | 50:50 | 700,000 |
| P-5 | CH₃ | CH₃ | $-C(=O)-NH_2$ | H | Cl⁻ | 50:50 | 100,000 |
| P-6 | CH₃ | CH₃ | $-C(=O)-NH_2$ | H | Cl⁻ | 50:50 | 50,000 |

TABLE 1-2

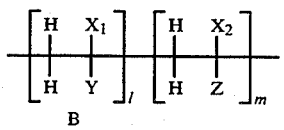

| No. | Y | Z | X1 | X2 | B | l:m | MW |
|---|---|---|---|---|---|---|---|
| P-7 | $-C(=O)-O-(CH_2)_2-N^+(CH_3)_3$ | $-C(=O)-NH_2$ | H | H | Cl⁻ | 50:50 | 200,000 |
| P-8 | $-C(=O)-NH(CH_2)_3-N^+(CH_3)_3$ | $-C(=O)-NH_2$ | H | H | Cl⁻ | 50:50 | 200,000 |
| P-9 | $-C_6H_4-CH_2-N^+(CH_3)_3$ | $-C(=O)-NH_2$ | H | H | Cl⁻ | 50:50 | 200,000 |
| P-10 | (N-methylpyrrolium group) | $-C(=O)-NH_2$ | H | H | Cl⁻ | 50:50 | 200,000 |

TABLE 1-2-continued $$\left[\begin{array}{cc} H & X_1 \\ H & Y \end{array}\right]_l \left[\begin{array}{cc} H & X_2 \\ H & Z \end{array}\right]_m$$
$$B$$

| No. | Y | Z | X1 | X2 | B | l:m | MW |
|---|---|---|---|---|---|---|---|
| P-11 | -CH₂-(1-methylimidazolium-3-yl) | -C(=O)-NH₂ | H | H | Cl⁻ | 50:50 | 200,000 |
| P-12 | 4-(1-methylpyridinium-1-yl) | -C(=O)-NH₂ | H | H | Cl⁻ | 50:50 | 200,000 |

TABLE 1-3

$$\left[\begin{array}{cc} H & X_1 \\ H & Y \end{array}\right]_l \left[\begin{array}{cc} H & X_2 \\ H & Z \end{array}\right]_m$$
$$B$$

| No. | Y | Z | X1 | X2 | B | l:m | MW |
|---|---|---|---|---|---|---|---|
| P-13 | -C(=O)-O-(CH₂)₂-N⁺(CH₃)₃ | -C(=O)-NH₂ | H | CH₃ | Cl⁻ | 50:50 | 100,000 |
| P-14 | -C(=O)-NH(CH₂)₃-N⁺(CH₃)₃ | -C(=O)-NH₂ | H | CH₃ | Cl⁻ | 50:50 | 100,000 |
| P-15 | -C₆H₄-CH₂-N⁺(CH₃)₃ | -C(=O)-NH₂ | H | CH₃ | Cl⁻ | 50:50 | 100,000 |
| P-16 | (1-methylimidazolium-3-yl) | -C(=O)-NH₂ | H | CH₃ | Cl⁻ | 50:50 | 100,000 |
| P-17 | -CH₂-(1-methylimidazolium-3-yl) | -C(=O)-NH₂ | H | CH₃ | Cl⁻ | 50:50 | 100,000 |
| P-18 | 4-(1-methylpyridinium-1-yl) | -C(=O)-NH₂ | H | CH₃ | Cl⁻ | 50:50 | 100,000 |

TABLE 1-4

[structure: pyrrolidinium copolymer with dimethyl N+ and B⁻ counterion, copolymerized with -[CH₂-CH(X₂)(Z)]- units]

| No. | Z | X2 | B⁻ | l:m | MW |
|---|---|---|---|---|---|
| P-19 | -C(=O)-NH₂ | H | Cl⁻ | 50:50 | 200,000 |
| P-20 | -C(=O)-NH₂ | CH₃ | Cl⁻ | 50:50 | 200,000 |
| P-21 | phenyl | H | Cl⁻ | 50:50 | 200,000 |

TABLE 1-4-continued

| No. | Z | X2 | B⁻ | l:m | MW |
|---|---|---|---|---|---|
| P-22 | phenyl | CH₃ | Cl⁻ | 50:50 | 200,000 |
| P-23 | 2-pyrrolidinone (N-linked) | H | Cl⁻ | 50:50 | 200,000 |

TABLE 1-5

[structure: copolymer -[CH₂-CH(X₁)(Y)]$_l$-[CH₂-CH(X₂)(Z)]$_m$- with counterion B]

| No. | Y | Z | X1 | X2 | B | l:m | MW |
|---|---|---|---|---|---|---|---|
| P-24 | 1-methyl-4-pyridinium | -C(=O)-NH₂ | H | H | Cl⁻ | 50:50 | 50,000 |
| P-25 | 1-methyl-4-pyridinium | -C(=O)-NH₂ | H | H | Br⁻ | 50:50 | 50,000 |
| P-26 | 1-methyl-4-pyridinium | -C(=O)-NH₂ | H | H | CH₃SO₄⁻ | 50:50 | 50,000 |
| P-27 | 1-methyl-4-pyridinium | -C(=O)-NH₂ | H | H | C₂H₅SO₄⁻ | 50:50 | 50,000 |
| P-28 | 1-methyl-4-pyridinium | -C(=O)-NH₂ | H | H | NO₃⁻ | 50:50 | 50,000 |

TABLE 1-5-continued $$\left[\begin{array}{cc} H & X_1 \\ | & | \\ H & Y \end{array}\right]_l \left[\begin{array}{cc} H & X_2 \\ | & | \\ H & Z \end{array}\right]_m$$
B

| No. | Y | Z | X1 | X2 | B | l:m | MW |
|---|---|---|---|---|---|---|---|
| P-29 | 4-methyl-1-methylpyridinium | -C(=O)-NH₂ | H | H | (CH₃)₂PO₄⁻ | 50:50 | 50,000 |

EXAMPLE 1

A 20% emulsifiable concentrate of commercially available sethoxydim was diluted with water so as to give a dosage of sethoxydim of 15 g/10a. Furthermore, a 40% liquid formulation of bentazone was diluted with water so as to give a dosage of bentazone of 200 g/10a. These diluted liquids were mixed and to the mixture was added the quaternary ammonium salt-containing polymeric compound as the antagonism inhibitor at a concentration of 0.5% by weight on the basis of the amount of the mixture. The resulting composition was applied (sprayed) at a rate of 50 l/10a.

This application amount corresponded to dosages of 15 g, 200 g and 250 g per 10a of sethoxydim and bentazone and the antagonism inhibitor, respectively.

Furthermore, a comparative test of applying only the mixture of sethoxydim and bentazone was conducted.

Test plants and the growing stage of the test plants when the composition was applied are as follows.

| Edible barnyard grass | 4.5–5 leaf stage |
|---|---|
| Green fox tail | 4.5–5 leaf stage |
| Shattercane | 4.5–5 leaf stage |

The application method was spraying method.

The herbicidal effect was visually evaluated on 20th day after application.

When the weeds were completely killed, this was graded to be 100 and when no weeds were killed (namely, no application of the herbicides), this was graded to be 0.

The results are shown in Table 2.

TABLE 2

| Kind of agents | Dosage g/10a | Edible barnyard grass | Green fox tail | Shattercane |
|---|---|---|---|---|
| Test section |  |  |  |  |
| Sethoxydim | 15 |  |  |  |
| Bentazon | 200 | 75 | 70 | 65 |
| P - 1 | 250 |  |  |  |
| Sethoxydim | 15 |  |  |  |
| Bentazone | 200 | 75 | 75 | 65 |
| P - 2 | 250 |  |  |  |
| Sethoxydim | 15 |  |  |  |
| Bentazon | 200 | 70 | 70 | 60 |
| P - 3 | 250 |  |  |  |
| Sethoxydim | 15 |  |  |  |
| Bentazone | 200 | 75 | 75 | 65 |
| P - 4 | 250 |  |  |  |
| Sethoxydim | 15 |  |  |  |
| Bentazon | 200 | 75 | 70 | 50 |
| P - 5 | 250 |  |  |  |
| Sethoxdim | 15 |  |  |  |
| Bentazon | 200 | 75 | 70 | 60 |
| P - 6 | 250 |  |  |  |
| Control section |  |  |  |  |
| Sethoxydim | 15 | 55 | 55 | 40 |
| Bentazon | 200 |  |  |  |

EXAMPLE 2

Herbicidal tests were conducted in the same manner as in Example 1 except that 35% emulsifiable concentrate of commercially available fluazifop-butyl was used in place of the 20% emulsifiable concentrate of sethoxydim.

Dosages of the herbicides and the antagonism inhibitor per 10a were as follows.

| Fluazifop-butyl | 15 g |
|---|---|
| Bentazone | 200 g |
| Antagonism inhibitor | 250 g |

Separately, a comarative test of applying only the mixture of fluazifop-butyl and bentazone was conducted as comparative control section.

The results are shown in Table 3.

TABLE 3

| Kind of agents | Dosage g/10a | Edible barnyard grass | Green fox tail | Shattercane |
|---|---|---|---|---|
| Test section |  |  |  |  |
| Fluazifop-butyl | 15 |  |  |  |
| Bentazon | 200 | 75 | 70 | 65 |
| P - 1 | 250 |  |  |  |
| Fluazifop-butyl | 15 |  |  |  |
| Bentazon | 200 | 80 | 75 | 65 |
| P - 2 | 250 |  |  |  |
| Fluazifop-butyl | 15 |  |  |  |
| Bentazon | 200 | 75 | 75 | 65 |
| P - 3 | 250 |  |  |  |
| Fluazifop-butyl | 15 |  |  |  |
| Bentazon | 200 | 75 | 75 | 60 |
| P - 4 | 250 |  |  |  |
| Fluazifop-butyl | 15 |  |  |  |

TABLE 3-continued

| Kind of agents | Dosage g/10a | Controlling effect | | |
|---|---|---|---|---|
| | | Edible barnyard grass | Green fox tail | Shatter-cane |
| Bentazon | 200 | 75 | 75 | 60 |
| p - 5 | 250 | | | |
| Fluazifop-butyl | 15 | | | |
| Bentazon | 200 | 75 | 70 | 60 |
| P - 6 | 250 | | | |
| Control section | | | | |
| Fluazifop-butyl | 15 | 55 | 55 | 40 |
| Bentazon | 200 | | | |

EXAMPLE 3

Herbicidal tests were conducted in the same manner as in Example 1 except that 20% liquid formation of commercially available imazaquin was used in place of bentazone.

Dosages of the herbicides and the antagonism inhibitor per 10a were as follows.

| | |
|---|---|
| Sethoxydim | 15 g |
| Imazaquin | 50 g |
| Antagonism inhibitor | 250 g |

Separately, a comarative test of applying only the mixture of sethoxydim and imazaquin was conducted as a comparative control section.

The results are shown in Table 4.

TABLE 4

| Kind of agents | Dosage g/10a | Controlling effect | | |
|---|---|---|---|---|
| | | Edible barnyard grass | Green fox tail | Shatter-cane |
| Test section | | | | |
| Sethoxydim | 15 | | | |
| Imazaquin | 50 | 80 | 80 | 65 |
| P - 1 | 250 | | | |
| Sethoxydim | 15 | | | |
| Imazaquin | 50 | 75 | 75 | 65 |
| P - 2 | 250 | | | |
| Sethoxydim | 15 | | | |
| Imazaquin | 50 | 75 | 75 | 60 |
| P - 3 | 250 | | | |
| Sethoxydim | 15 | | | |
| Imazaquin | 50 | 75 | 75 | 65 |
| P - 4 | 250 | | | |
| Sethoxydim | 15 | | | |
| Imazaquin | 50 | 80 | 75 | 65 |
| P - 5 | 250 | | | |
| Sethoxydim | 15 | | | |
| Imazaquin | 50 | 75 | 70 | 65 |
| P - 6 | 250 | | | |
| Control section | | | | |
| Sethoxydim | 15 | 65 | 65 | 50 |
| Imazaquin | 50 | | | |

EXAMPLE 4

A 20% emulsifiable concentrate of commercially available sethoxydim was diluted with water so as to give a dosage of sethoxydim of 30 g/10a. Furthermore, a 40% liquid formulation of bentazone was diluted with water so as to give a dosage of bentazone of 100 g/10a. These diluted liquids were mixed and to the mixture was added the quaternary ammonium salt-containing polymeric compound as the antagonism inhibitor and each of the fatty acids or derivatives thereof shown in Table 5 at a concentration of 0.2% by weight and 1% by weight on the basis of the amount of the mixture, respectively. The resulting compositions were applied (sprayed) at a rate of 20 l /10a.

Test method was the same as in Example 1 except that comparative tests of applying a mixture of sethoxydim, bentazone and the P-1 in Table 1 was conducted and the growing stage of the test plants was 4 leaf stage.

The results are shown in Tables 6, 7 and 8.

TABLE 5

| Fatty acids and derivatives thereof ($R_6COOR_7$) | | |
|---|---|---|
| Marks | $R_6$ | $R_7$ |
| FA - 1 | $C_{11}H_{23}$ | H |
| FA - 2 | $C_{13}H_{27}$ | H |
| FA - 3 | $C_{15}H_{31}$ | H |
| FA - 4 | $C_{17}H_{35}$ | H |
| FA - 5 | $C_{17}H_{33}$ | H |
| FA - 6 | $C_{17}H_{31}$ | H |
| FA - 7 | $C_{17}H_{29}$ | H |
| FA - 8 | $C_{21}H_{43}$ | H |
| FA - 9 | $C_{11}H_{23}$ | $CH_3$ |
| FA - 10 | $C_{15}H_{33}$ | $CH_3$ |
| FA - 11 | $C_{17}H_{33}$ | $CH_3$ |
| FA - 12 | $C_{11}H_{23}$ | $C_2H_5$ |
| FA - 13 | $C_{15}H_{33}$ | $C_2H_5$ |
| FA - 14 | $C_{17}H_{33}$ | $C_2H_5$ |
| FA - 15 | $C_{15}H_{33}$ | $C_8H_{17}$ |
| FA - 16 | $C_{17}H_{33}$ | $C_8H_{17}$ |

TABLE 6

| Kind of agents | Dosage g/10a | Controlling effect | | |
|---|---|---|---|---|
| | | Edible barnyard grass | Green fox tail | Shatter-cane |
| Test section | | | | |
| Sethoxydim | 30 | | | |
| Bentazon | 100 | 100 | 100 | 100 |
| P - 1 | 40 | | | |
| FA - 1 | 200 | | | |
| Sethoxydim | 30 | | | |
| Bentazon | 100 | 100 | 100 | 100 |
| P - 1 | 40 | | | |
| FA - 2 | 200 | | | |
| Sethoxydim | 30 | | | |
| Bentazon | 100 | 100 | 100 | 100 |
| P - 1 | 40 | | | |
| FA - 3 | 200 | | | |
| Sethoxydim | 30 | | | |
| Bentazon | 100 | 100 | 100 | 100 |
| P - 1 | 40 | | | |
| FA - 4 | 200 | | | |
| Sethoxydim | 30 | | | |
| Bentazon | 100 | 100 | 100 | 100 |
| P - 1 | 40 | | | |
| FA - 5 | 200 | | | |
| Sethoxydim | 30 | | | |
| Bentazon | 100 | 100 | 100 | 100 |
| P - 1 | 40 | | | |
| FA - 6 | 200 | | | |
| Sethoxydim | 30 | | | |
| Bentazon | 100 | 100 | 100 | 100 |
| P - 1 | 40 | | | |
| FA - 7 | 200 | | | |

TABLE 7

| Kind of agents | Dosage g/10a | Controlling effect | | |
|---|---|---|---|---|
| | | Edible barnyard grass | Green fox tail | Shatter-cane |
| Test section | | | | |
| Sethoxydim | 30 | | | |
| Bentazon | 100 | 100 | 100 | 100 |
| P - 1 | 40 | | | |
| FA - 8 | 200 | | | |
| Sethoxydim | 30 | | | |

TABLE 7-continued

| Kind of agents | Dosage g/10a | Controlling effect | | |
|---|---|---|---|---|
| | | Edible barnyard grass | Green fox tail | Shatter-cane |
| Bentazon | 100 | 100 | 100 | 100 |
| P - 1 | 40 | | | |
| FA - 9 | 200 | | | |
| Sethoxydim | 30 | | | |
| Bentazon | 100 | 100 | 100 | 100 |
| P - 1 | 40 | | | |
| FA - 10 | 200 | | | |
| Sethoxydim | 30 | | | |
| Bentazon | 100 | 100 | 100 | 100 |
| P - 1 | 40 | | | |
| FA - 11 | 200 | | | |
| Sethoxydim | 30 | | | |
| Bentazon | 100 | 100 | 100 | 100 |
| P - 1 | 40 | | | |
| FA - 12 | 200 | | | |
| Sethoxydim | 30 | | | |
| Bentazon | 100 | 100 | 100 | 100 |
| P - 1 | 40 | | | |
| FA - 13 | 200 | | | |
| Sethoxydim | 30 | | | |
| Bentazon | 100 | 100 | 100 | 100 |
| P - 1 | 40 | | | |
| FA - 14 | 200 | | | |

TABLE 8

| Kind of agents | Dosage g/10a | Controlling effect | | |
|---|---|---|---|---|
| | | Edible barnyard grass | Green fox tail | Shatter-cane |
| Test section | | | | |
| Sethoxydim | 30 | | | |
| Bentazon | 100 | 100 | 100 | 100 |
| P - 1 | 40 | | | |
| FA - 15 | 200 | | | |
| Sethoxydim | 30 | | | |
| Bentazon | 100 | 100 | 100 | 100 |
| P - 1 | 40 | | | |
| FA - 16 | 200 | | | |
| Control section | | | | |
| Sethoxydim | 30 | 70 | 70 | 65 |
| Bentazon | 100 | | | |
| Sethoxydim | 30 | | | |
| Bentazon | 100 | 90 | 90 | 85 |
| P - 1 | 40 | | | |

EXAMPLE 5

Example 4 was repeated except that 35% emulsifiable concentrate of commercially available fluazifop-butyl was used in place of the 20% emulsifiable concentrate of sethoxydim.

Dosages of the herbicides, the antagonism inhibitor and the fatty acids or derivatives thereof per 10a were as follows.

| | |
|---|---|
| Fluazifop-butyl | 30 g |
| Bentazone | 100 g |
| Antagonism inhibitor | 40 g |
| Fatty acid or derivative thereof | 200 g |

The results are shown in Tables 9, 10 and 11.

TABLE 9

| Kind of agents | Dosage g/10a | Controlling effect | | |
|---|---|---|---|---|
| | | Edible barnyard grass | Green fox tail | Shatter-cane |
| Test section | | | | |
| Fluazifop-butyl | 30 | | | |
| Bentazon | 100 | 100 | 100 | 100 |
| P - 1 | 40 | | | |
| FA - 1 | 200 | | | |
| Fluazifop-butyl | 30 | | | |
| Bentazon | 100 | 100 | 100 | 100 |
| P - 1 | 40 | | | |
| FA - 2 | 200 | | | |
| Fluazifop-butyl | 30 | | | |
| Bentazon | 100 | 100 | 100 | 100 |
| P - 1 | 40 | | | |
| FA - 3 | 200 | | | |
| Fluazifop-butyl | 30 | | | |
| Bentazon | 100 | 100 | 100 | 100 |
| P - 1 | 40 | | | |
| FA - 4 | 200 | | | |
| Fluazifop-butyl | 30 | | | |
| Bentazon | 100 | 100 | 100 | 100 |
| P - 1 | 40 | | | |
| FA - 5 | 200 | | | |
| Fluazifop-butyl | 30 | | | |
| Bentazon | 100 | 100 | 100 | 100 |
| P - 1 | 40 | | | |
| FA - 6 | 200 | | | |
| Fluazifop-butyl | 30 | | | |
| Bentazon | 100 | 100 | 100 | 100 |
| P - 1 | 40 | | | |
| FA - 7 | 200 | | | |

TABLE 10

| Kind of agents | Dosage g/10a | Controlling effect | | |
|---|---|---|---|---|
| | | Edible barnyard grass | Green fox tail | Shatter-cane |
| Test section | | | | |
| Fluazifop-butyl | 30 | | | |
| Bentazon | 100 | 100 | 100 | 100 |
| P - 1 | 40 | | | |
| FA - 8 | 200 | | | |
| Fluazifop-butyl | 30 | | | |
| Bentazon | 100 | 100 | 100 | 100 |
| P - 1 | 40 | | | |
| FA - 9 | 200 | | | |
| Fluazifop-butyl | 30 | | | |
| Bentazon | 100 | 100 | 100 | 100 |
| P - 1 | 40 | | | |
| FA - 10 | 200 | | | |
| Fluazifop-butyl | 30 | | | |
| Bentazon | 100 | 100 | 100 | 100 |
| P - 1 | 40 | | | |
| FA - 11 | 200 | | | |
| Fluazifop-butyl | 30 | | | |
| Bentazon | 100 | 100 | 100 | 100 |
| P - 1 | 40 | | | |
| FA - 12 | 200 | | | |
| Fluazifop-butyl | 30 | | | |
| Bentazon | 100 | 100 | 100 | 100 |
| P - 1 | 40 | | | |
| FA - 13 | 200 | | | |
| Fluazifop-butyl | 30 | | | |
| Bentazon | 100 | 100 | 100 | 100 |
| P - 1 | 40 | | | |
| FA - 14 | 200 | | | |

TABLE 11

| Kind of agents | Dosage g/10a | Controlling effect | | |
|---|---|---|---|---|
| | | Edible barnyard grass | Green fox tail | Shatter-cane |
| Test section | | | | |
| Fluazifop-butyl | 30 | | | |

TABLE 11-continued

| Kind of agents | Dosage g/10a | Controlling effect | | |
|---|---|---|---|---|
| | | Edible barnyard grass | Green fox tail | Shatter-cane |
| Bentazon | 100 | 100 | 100 | 100 |
| P - 1 | 40 | | | |
| FA - 15 | 200 | | | |
| Fluazifop-butyl | 30 | | | |
| Bentazon | 100 | 100 | 100 | 100 |
| P - 1 | 40 | | | |
| FA - 16 | 200 | | | |
| Control section | | | | |
| Fluazifop-butyl | 30 | 70 | 70 | 65 |
| Bentazon | 100 | | | |
| Fluazifop-butyl | 30 | | | |
| Bentazon | 100 | 90 | 90 | 85 |
| P - 1 | 40 | | | |

EXAMPLE 6

Example 4 was repeated except that mineral oil was used in place of the fatty acid and the derivative thereof.

As an emulsifier for the mineral oil, SORPOL 8283 (manufactured by Toho Chemical Co., Ltd.) was added in an amount of 0.2% by weight of the spraying solution. This emulsifier gives no adverse effect on the antagonism inhibiting action of the antagonism inhibitor and the herbicidal action of the herbicidal composition and on the growing of the crop.

The results are shown in Table 12.

TABLE 12

| Kind of agents | Dosage g/10a | Controlling effect | | |
|---|---|---|---|---|
| | | Edible barnyard grass | Green fox tail | Shatter-cane |
| Test section | | | | |
| Sethoxydim | 30 | | | |
| Bentazon | 100 | 100 | 100 | 100 |
| P - 1 | 40 | | | |
| PO - 1[1)] | 200 | | | |
| Sethoxydim | 30 | | | |
| Bentazon | 100 | 100 | 100 | 100 |
| P - 1 | 40 | | | |
| PO - 2[2)] | 200 | | | |
| Control section | | | | |
| Sethoxydim | 30 | 70 | 70 | 65 |
| Bentazon | 100 | | | |
| Sethoxydim | 30 | | | |
| Bentazon | 100 | 90 | 90 | 85 |
| P - 1 | 40 | | | |

[1)]Machine oil base
[2)]Spindle oil base

EXAMPLE 7

Example 6 was repeated except that 35% emulsifiable concentrate of commercially available fluazifop-butyl was used in place of the 20% emulsifiable concentrate of sethoxydim.

Dosages of the herbicides, the antagonism inhibitor and the mineral oil per 10a were as follows.

| Fluazifop-butyl | 30 g |
|---|---|
| Bentazone | 100 g |
| Antagonism inhibitor | 40 g |
| Mineral oil | 200 g |

The results are shown in Table 13.

TABLE 13

| Kind of agents | Dosage g/10a | Controlling effect | | |
|---|---|---|---|---|
| | | Edible barnyard grass | Green fox tail | Shatter-cane |
| Test section | | | | |
| Fluazifop-butyl | 30 | | | |
| Bentazon | 100 | 100 | 100 | 100 |
| P - 1 | 40 | | | |
| PO - 1[1)] | 200 | | | |
| Fluazifop-butyl | 30 | | | |
| Bentazon | 100 | 100 | 100 | 100 |
| P - 1 | 40 | | | |
| PO - 2[2)] | 200 | | | |
| Control section | | | | |
| Fluazifop-butyl | 30 | 70 | 70 | 65 |
| Bentazon | 100 | | | |
| Fluazifop-butyl | 30 | | | |
| Bentazon | 100 | 90 | 90 | 85 |
| P - 1 | 40 | | | |

[1)]Machine oil base
[2)]Spindle oil base

EXAMPLE 8

Example 4 was repeated except that liquid fertilizer was used in place of the fatty acid and the derivative thereof in an amount of 2.5% by weight based on the amount of the application solution.

The results are shown in Tables 14 and 15.

TABLE 14

| Kind of agents | Dosage g/10a | Controlling effect | | |
|---|---|---|---|---|
| | | Edible barnyard grass | Green fox tail | Shatter-cane |
| Test section | | | | |
| Sethoxydim | 30 | | | |
| Bentazon | 100 | 100 | 100 | 100 |
| P - 1 | 40 | | | |
| LF - 1[1)] | 500 | | | |
| Sethoxydim | 30 | | | |
| Bentazon | 100 | 100 | 100 | 100 |
| P - 1 | 40 | | | |
| LF - 2[2)] | 500 | | | |
| Sethoxydim | 30 | | | |
| Bentazon | 100 | 100 | 100 | 100 |
| P - 1 | 40 | | | |
| LF - 3[3)] | 500 | | | |
| Sethoxydim | 30 | | | |
| Bentazon | 100 | 100 | 100 | 100 |
| P - 1 | 40 | | | |
| LF - 4[4)] | 500 | | | |

[1)]Urea
[2)]Ammonium nitrate
[3)]Ammonium sulfate
[4)]Ammonium phosphate

TABLE 15

| Kind of agents | Dosage g/10a | Controlling effect | | |
|---|---|---|---|---|
| | | Edible barnyard grass | Green fox tail | Shatter-cane |
| Test section | | | | |
| Sethoxydim | 30 | | | |
| Bentazon | 100 | 100 | 100 | 100 |
| P - 1 | 40 | | | |
| LF - 5[5)] | 500 | | | |
| Control section | | | | |
| Sethoxydim | 30 | 70 | 70 | 65 |
| Bentazon | 100 | | | |
| Sethoxydim | 30 | | | |
| Bentazon | 100 | 90 | 90 | 85 |

TABLE 15-continued

| Kind of agents | Dosage g/10a | Controlling effect | | |
|---|---|---|---|---|
| | | Edible barnyard grass | Green fox tail | Shatter- cane |
| P - 1 | 40 | | | |

[5] Urea + ammonium nitrate

EXAMPLE 9

Example 8 was repeated except that 35% emulsifiable concentrate of commercially available fluazifop-butyl was used in place of the 20% emulsifiable concentrate of sethoxydim.

Dosages of the herbicides, the antagonism inhibitor and the liquid fertilizer per 10a were as follows.

| Fluazifop-butyl | 30 g |
|---|---|
| Bentazone | 100 g |
| Antagonism inhibitor | 40 g |
| Liquid fertilizer | 500 g |

The results are shown in Tables 16 and 17.

TABLE 16

| Kind of agents | Dosage g/10a | Controlling effect | | |
|---|---|---|---|---|
| | | Edible barnyard grass | Green fox tail | Shatter- cane |
| Test section | | | | |
| Fluazifop-butyl | 30 | | | |
| Bentazon | 100 | 100 | 100 | 100 |
| P - 1 | 40 | | | |
| LF - 1[1] | 500 | | | |
| Fluazifop-butyl | 30 | | | |
| Bentazon | 100 | 100 | 100 | 100 |
| P - 1 | 40 | | | |
| LF - 2[2] | 500 | | | |
| Fluazifop-butyl | 30 | | | |
| Bentazon | 100 | 100 | 100 | 100 |
| P - 1 | 40 | | | |
| LF - 3[3] | 500 | | | |
| Fluazifop-butyl | 30 | | | |
| Bentazon | 100 | 100 | 100 | 100 |
| P - 1 | 40 | | | |
| LF - 4[4] | 500 | | | |

[1] Urea
[2] Ammonium nitrate
[3] Ammonium sulfate
[4] Ammonium phosphate

TABLE 17

| Kind of agents | Dosage g/10a | Controlling effect | | |
|---|---|---|---|---|
| | | Edible barnyard grass | Green fox tail | Shatter- cane |
| Test section | | | | |
| Fluazifop-butyl | 30 | | | |
| Bentazon | 100 | 100 | 100 | 100 |
| P - 1 | 40 | | | |
| LF - 5[5] | 500 | | | |
| Control section | | | | |
| Fluazifop-butyl | 30 | | | |
| Bentazon | 100 | 70 | 70 | 65 |
| Fluazifop-butyl | 30 | | | |
| Bentazon | 100 | 90 | 90 | 85 |
| P - 1 | 40 | | | |

[5] Urea + Ammonium nitrate

EXAMPLE 10

Example 4 was repeated except that surface active agent was used in place of the fatty acid and the derivative thereof in an amount of 0.5% by weight based on the amount of the application solution.

The results are shown in Tables 18 and 19.

TABLE 18

| Kind of agents | Dosage g/10a | Controlling effect | | |
|---|---|---|---|---|
| | | Edible barnyard grass | Green fox tail | Shatter- cane |
| Test section | | | | |
| Sethoxydim | 30 | | | |
| Bentazon | 100 | 95 | 95 | 90 |
| P - 1 | 40 | | | |
| SAA - 1[1] | 100 | | | |
| Sethoxydim | 30 | | | |
| Bentazon | 100 | 95 | 95 | 90 |
| P - 1 | 40 | | | |
| SAA - 2[2] | 100 | | | |
| Sethoxydim | 30 | | | |
| Bentazon | 100 | 95 | 95 | 90 |
| P - 1 | 40 | | | |
| SAA - 3[3] | 100 | | | |
| Sethoxydim | 30 | | | |
| Bentazon | 100 | 95 | 95 | 90 |
| P - 1 | 40 | | | |
| SAA - 4[4] | 100 | | | |

[1] POE (8) Octylphenol ether
[2] POE (10) Nonylphenol ether
[3] POE (14) Oleate
[4] POE (14) Resinate

TABLE 19

| Kind of agents | Dosage g/10a | Controlling effect | | |
|---|---|---|---|---|
| | | Edible barnyard grass | Green fox tail | Shatter- cane |
| Test section | | | | |
| Sethoxydim | 30 | | | |
| Bentazon | 100 | 95 | 95 | 90 |
| P - 1 | 40 | | | |
| SAA - 5[5] | 100 | | | |
| Sethoxydim | 30 | | | |
| Bentazon | 100 | 95 | 95 | 90 |
| P - 1 | 40 | | | |
| SAA - 6[6] | 100 | | | |
| Sethoxydim | 30 | | | |
| Bentazon | 100 | 95 | 95 | 90 |
| P - 1 | 40 | | | |
| SAA - 7[7] | 100 | | | |
| Control section | | | | |
| Sethoxydim | 30 | 70 | 70 | 65 |
| Bentazon | 100 | | | |
| Sethoxydim | 30 | | | |
| Bentazon | 100 | 90 | 90 | 85 |
| P - 1 | 40 | | | |

[5] POE (12) Tridecyl alcohol ether
[6] Lauric acid amide propyl betaine
[7] 2-Lauryl-N-carboxymethyl-N-hydroxyethylimidazolinium-betaine

EXAMPLE 11

Example 10 was repeated except that 35% emulsifiable concentrate of commercially available fluazifop-butyl was used in place of the 20% emulsifiable concentrate of sethoxydim.

Dosages of the herbicides, the antagonism inhibitor and the surface active agent per 10a were as follows.

| Fluazifop-butyl | 30 g |
|---|---|
| Bentazone | 100 g |
| Antagonism inhibitor | 40 g |
| Surface active agent | 100 g |

The results are shown in Tables 20 and 21.

TABLE 20

| Kind of agents | Dosage g/10a | Controlling effect | | |
|---|---|---|---|---|
| | | Edible barnyard grass | Green fox tail | Shatter-cane |
| Test section | | | | |
| Fluazifop-butyl | 30 | | | |
| Bentazon | 100 | 95 | 95 | 90 |
| P - 1 | 40 | | | |
| SAA - 1[1)] | 100 | | | |
| Fluazifop-butyl | 30 | | | |
| Bentazon | 100 | 95 | 95 | 90 |
| P - 1 | 40 | | | |
| SAA - 2[2)] | 100 | | | |
| Fluazifop-butyl | 30 | | | |
| Bentazon | 100 | 95 | 95 | 90 |
| P - 1 | 40 | | | |
| SAA - 3[3)] | 100 | | | |
| Fluazifop-butyl | 30 | | | |
| Bentazon | 100 | 95 | 95 | 90 |
| P - 1 | 40 | | | |
| SAA - 4[4)] | 100 | | | |

[1)] POE (8) Octylphenol ether
[2)] POE (10) Nonylphenol ether
[3)] POE (14) Oleate
[4)] POE (14) Resinate

TABLE 21

| Kind of agents | Dosage g/10a | Controlling effect | | |
|---|---|---|---|---|
| | | Edible barnyard grass | Green fox tail | Shatter-cane |
| Test section | | | | |
| Fluazifop-butyl | 30 | | | |
| Bentazon | 100 | 95 | 95 | 90 |
| P - 1 | 40 | | | |
| SAA - 5[5)] | 100 | | | |
| Fluazifop-butyl | 30 | | | |
| Bentazon | 100 | 95 | 95 | 90 |
| P - 1 | 40 | | | |
| SAA - 6[6)] | 100 | | | |
| Fluazifop-butyl | 30 | | | |
| Bentazon | 100 | 95 | 95 | 90 |
| P - 1 | 40 | | | |
| SAA - 7[7)] | 100 | | | |
| Control section | | | | |
| Fluazifop-butyl | 30 | | | |
| Bentazon | 100 | 70 | 70 | 65 |
| Fluazifop-butyl | 30 | | | |
| Bentazon | 100 | 90 | 90 | 85 |
| P - 1 | 40 | | | |

[5)] POE (12) Tridecyl alcohol ether
[6)] Lauric acid amide propyl betaine
[7)] 2-Lauryl-N-carboxymethyl-N-hydroxyethylimidazolinium-betaine

EXAMPLE 12

A 20% emulsifiable concentrate of commercially available sethoxydim was diluted with water so as to give a dosage of sethoxydim of 15 g/10a. Furthermore, a 40% liquid formulation of commercially available bentazon was diluted with water so as to give a dosage of betazon of 80 g/10a. These diluted liquids were mixed, and to the mixture was added the quaternary ammonium salt-containing polymeric compound as the antagonism inhibitor at a concentration of 0.1% by weight on the basis of the amount of the liquid to be applied. The resulting composition was applied (sprayed) at a rate of 18.7 liters/10a.

This application amount corresponded to dosage of 15 g, 80 g and 18.7 g per 10a of sethoxydim, bentazon and the antagonism inhibitor, respectively.

Furthermore, comparative tests of applying only the mixture of sethoxydim and bentazon were conducted.

Test plants and their growing stages when the composition was applied to were as follows.

| Edible barnyard grass | 4.5–5 leaf stage |
|---|---|
| Green fox tail | 4.5–5 leaf stage |
| Shattercane | 4.5–5 leaf strage |

The application method was spraying.

The herbicidal effect was visually evaluated on 20th day after the application. When the weeds were completely killed, this was graded to be 100, and when no weeds were killed (namely, no application of the herbicides), this was graded to be 0.

The results are shown in Tables 22-1, 22-2, 22-3 and 22-4.

TABLE 22-1

| | Dosage g/10a | Herbicidal effect | | |
|---|---|---|---|---|
| | | Edible barn-yard grass | Green fox tail | Shatter-cane |
| Examples | | | | |
| sethoxydim | 15 | | | |
| bentazon | 80 | 85 | 80 | 80 |
| P-7 | 18.7 | | | |
| sethoxydim | 15 | | | |
| bentazon | 80 | 85 | 80 | 80 |
| P-8 | 18.7 | | | |
| sethoxydim | 15 | | | |
| bentazon | 80 | 85 | 80 | 80 |
| P-9 | 18.7 | | | |
| sethoxydim | 15 | | | |
| bentazon | 80 | 85 | 80 | 80 |
| P-10 | 18.7 | | | |
| sethoxydim | 15 | | | |
| bentazon | 80 | 85 | 80 | 80 |
| P-11 | 18.7 | | | |
| sethoxydim | 15 | | | |
| bentazon | 80 | 85 | 80 | 80 |
| P-12 | 18.7 | | | |
| sethoxydim | 15 | | | |
| bentazon | 80 | 55 | 55 | 45 |

TABLE 22-2

| | Dosage g/10a | Herbicidal effect | | |
|---|---|---|---|---|
| | | Edible barn-yard grass | Green fox tail | Shatter-cane |
| Examples | | | | |
| sethoxydim | 15 | | | |
| bentazon | 80 | 85 | 80 | 80 |
| P-13 | 18.7 | | | |
| sethoxydim | 15 | | | |
| bentazon | 80 | 85 | 80 | 80 |
| P-14 | 18.7 | | | |
| sethoxydim | 15 | | | |
| bentazon | 80 | 85 | 80 | 80 |
| P-15 | 18.7 | | | |
| sethoxydim | 15 | | | |
| bentazon | 80 | 85 | 80 | 80 |
| P-16 | 18.7 | | | |
| sethoxydim | 15 | | | |
| bentazon | 80 | 85 | 80 | 80 |
| P-17 | 18.7 | | | |
| sethoxydim | 15 | | | |
| bentazon | 80 | 85 | 80 | 80 |
| P-18 | 18.7 | | | |
| sethoxydim | 15 | | | |
| bentazon | 80 | 55 | 55 | 45 |

TABLE 22-3

| | Dosage g/10a | Herbicidal effect | | |
|---|---|---|---|---|
| | | Edible barn-yard grass | Green fox tail | Shatter-cane |
| Examples | | | | |

TABLE 22-3-continued

| | Dosage g/10a | Herbicidal effect | | |
|---|---|---|---|---|
| | | Edible barnyard grass | Green fox tail | Shattercane |
| sethoxydim | 15 | | | |
| bentazon | 80 | 85 | 80 | 80 |
| P-19 | 18.7 | | | |
| sethoxydim | 15 | | | |
| bentazon | 80 | 85 | 80 | 80 |
| P-20 | 18.7 | | | |
| sethoxydim | 15 | | | |
| bentazon | 80 | 85 | 80 | 80 |
| P-21 | 18.7 | | | |
| sethoxydim | 15 | | | |
| bentazon | 80 | 85 | 80 | 80 |
| P-22 | 18.7 | | | |
| sethoxydim | 15 | | | |
| bentazon | 80 | 85 | 80 | 80 |
| P-23 | 18.7 | | | |
| sethoxydim | 15 | | | |
| bentazon | 80 | 55 | 55 | 45 |

TABLE 22-4

| | Dosage g/10a | Herbicidal effect | | |
|---|---|---|---|---|
| | | Edible barnyard grass | Green fox tail | Shattercane |
| Examples | | | | |
| sethoxydim | 15 | | | |
| bentazon | 80 | 85 | 80 | 80 |
| P-24 | 18.7 | | | |
| sethoxydim | 15 | | | |
| bentazon | 80 | 85 | 80 | 80 |
| P-25 | 18.7 | | | |
| sethoxydim | 15 | | | |
| bentazon | 80 | 85 | 80 | 80 |
| P-26 | 18.7 | | | |
| sethoxydim | 15 | | | |
| bentazon | 80 | 85 | 80 | 80 |
| P-27 | 18.7 | | | |
| sethoxydim | 15 | | | |
| bentazon | 80 | 85 | 80 | 80 |
| P-28 | 18.7 | | | |
| sethoxydim | 15 | | | |
| bentazon | 80 | 85 | 80 | 80 |
| P-29 | 18.7 | | | |
| sethoxydim | 15 | | | |
| bentazon | 80 | 55 | 55 | 45 |

EXAMPLE 13

Herbicidal tests were conducted in the same manner as in Example 12 except that 20% liquid formulation of commercially available imazaquin was used in place of the 40% liquid formulation of bentazon.

Dosages of the herbicides and the antagonism inhibitor per 10a were as follows.

| | |
|---|---|
| Sethoxydim | 15 g |
| Imazaquin | 10 g |
| Antagonism inhibitor | 18.7 g |

Separately, comparative tests of applying only the mixture of sethoxydim and imazaquin were conducted as comparative control section.

The results are shown in Tables 23-1, 23-2, 23-3 and 23-4.

TABLE 23-1

| | Dosage g/10a | Herbicidal effect | | |
|---|---|---|---|---|
| | | Edible barnyard grass | Green fox tail | Shattercane |
| Examples | | | | |
| sethoxydim | 15 | | | |
| imazaquin | 10 | 70 | 65 | 60 |
| P-7 | 18.7 | | | |
| sethoxydim | 15 | | | |
| imazaquin | 10 | 70 | 65 | 60 |
| P-8 | 18.7 | | | |
| sethoxydim | 15 | | | |
| imazaquin | 10 | 70 | 65 | 60 |
| P-9 | 18.7 | | | |
| sethoxydim | 15 | | | |
| imazaquin | 10 | 70 | 65 | 60 |
| P-10 | 18.7 | | | |
| sethoxydim | 15 | | | |
| imazaquin | 10 | 70 | 65 | 60 |
| P-11 | 18.7 | | | |
| sethoxydim | 15 | | | |
| imazaquin | 10 | 70 | 65 | 60 |
| P-12 | 18.7 | | | |
| sethoxydim | 15 | | | |
| imazaquin | 10 | 50 | 50 | 45 |

TABLE 23-2

| | Dosage g/10a | Herbicidal effect | | |
|---|---|---|---|---|
| | | Edible barnyard grass | Green fox tail | Shattercane |
| Examples | | | | |
| sethoxydim | 15 | | | |
| imazaquin | 10 | 70 | 65 | 60 |
| P-13 | 18.7 | | | |
| sethoxydim | 15 | | | |
| imazaquin | 10 | 70 | 65 | 60 |
| P-14 | 18.7 | | | |
| sethoxydim | 15 | | | |
| imazaquin | 10 | 70 | 65 | 60 |
| P-15 | 18.7 | | | |
| sethoxydim | 15 | | | |
| imazaquin | 10 | 70 | 65 | 60 |
| P-16 | 18.7 | | | |
| sethoxydim | 15 | | | |
| imazaquin | 10 | 70 | 65 | 60 |
| P-17 | 18.7 | | | |
| sethoxydim | 15 | | | |
| imazaquin | 10 | 70 | 65 | 60 |
| P-18 | 18.7 | | | |
| sethoxydim | 15 | | | |
| imazaquin | 10 | 50 | 50 | 45 |

TABLE 23-3

| | Dosage g/10a | Herbicidal effect | | |
|---|---|---|---|---|
| | | Edible barnyard grass | Green fox tail | Shattercane |
| Examples | | | | |
| sethoxydim | 15 | | | |
| imazaquin | 10 | 70 | 65 | 60 |
| P-19 | 18.7 | | | |
| sethoxydim | 15 | | | |
| imazaquin | 10 | 70 | 65 | 60 |
| P-20 | 18.7 | | | |
| sethoxydim | 15 | | | |
| imazaquin | 10 | 70 | 65 | 60 |
| P-21 | 18.7 | | | |
| sethoxydim | 15 | | | |
| imazaquin | 10 | 70 | 65 | 60 |
| P-22 | 18.7 | | | |
| sethoxydim | 15 | | | |
| imazaquin | 10 | 70 | 65 | 60 |
| P-23 | 18.7 | | | |
| sethoxydim | 15 | | | |
| imazaquin | 10 | 50 | 50 | 45 |

TABLE 23-4

| Examples | Dosage g/10a | Herbicidal effect | | |
|---|---|---|---|---|
| | | Edible barn-yard grass | Green fox tail | Shatter-cane |
| sethoxydim | 15 | | | |
| imazaquin | 10 | 70 | 65 | 60 |
| P-24 | 18.7 | | | |
| sethoxydim | 15 | | | |
| imazaquin | 10 | 70 | 65 | 60 |
| P-25 | 18.7 | | | |
| sethoxydim | 15 | | | |
| imazaquin | 10 | 70 | 65 | 60 |
| P-26 | 18.7 | | | |
| sethoxydim | 15 | | | |
| imazaquin | 10 | 70 | 65 | 60 |
| P-27 | 18.7 | | | |
| sethoxydim | 15 | | | |
| imazaquin | 10 | 70 | 65 | 60 |
| P-28 | 18.7 | | | |
| sethoxydim | 15 | | | |
| imazaquin | 10 | 70 | 65 | 60 |
| P-29 | 18.7 | | | |
| sethoxydim | 15 | | | |
| imazaquin | 10 | 50 | 50 | 45 |

EXAMPLE 14

Herbicidal tests were conducted in the same manner as in Example 12 except that 20% liquid formulation of commerically available imazethapyr was used in place of the 40% liquid formulation of bentazon.

Dosage of the herbicides and the antagonism inhibitor per 10a were as follows.

| | |
|---|---|
| Sethoxydim | 15 g |
| Imazethapyr | 3 g |
| Antagonism inhibitor | 18.7 g |

Separately, comparative tests of applying only the mixture of sethoxydim and imazethapyr were conducted as comparative control section.

The results are shown in Tables 24-1, 24-2, 24-3 and 24-4.

TABLE 24-1

| Examples | Dosage g/10a | Herbicidal effect | | |
|---|---|---|---|---|
| | | Edible barn-yard grass | Green fox tail | Shatter-cane |
| sethoxydim | 15 | | | |
| imazethapyr | 3 | 70 | 65 | 60 |
| P-7 | 18.7 | | | |
| sethoxydim | 15 | | | |
| imazethapyr | 3 | 70 | 65 | 60 |
| P-8 | 18.7 | | | |
| sethoxydim | 15 | | | |
| imazethapyr | 3 | 70 | 65 | 60 |
| P-9 | 18.7 | | | |
| sethoxydim | 15 | | | |
| imazethapyr | 3 | 70 | 65 | 60 |
| P-10 | 18.7 | | | |
| sethoxydim | 15 | | | |
| imazethapyr | 3 | 70 | 65 | 60 |
| P-11 | 18.7 | | | |
| sethoxydim | 15 | | | |
| imazethapyr | 3 | 70 | 65 | 60 |
| P-12 | 18.7 | | | |
| sethoxydim | 15 | | | |
| imazethapyr | 3 | 50 | 50 | 45 |

TABLE 24-2

| Examples | Dosage g/10a | Herbicidal effect | | |
|---|---|---|---|---|
| | | Edible barn-yard grass | Green fox tail | Shatter-cane |
| sethoxydim | 15 | | | |
| imazethapyr | 3 | 70 | 65 | 60 |
| P-13 | 18.7 | | | |
| sethoxydim | 15 | | | |
| imazethapyr | 3 | 70 | 65 | 60 |
| P-14 | 18.7 | | | |
| sethoxydim | 15 | | | |
| imazethapyr | 3 | 70 | 65 | 60 |
| P-15 | 18.7 | | | |
| sethoxydim | 15 | | | |
| imazethapyr | 3 | 70 | 65 | 60 |
| P-16 | 18.7 | | | |
| sethoxydim | 15 | | | |
| imazethapyr | 3 | 70 | 65 | 60 |
| P-17 | 18.7 | | | |
| sethoxydim | 15 | | | |
| imazethapyr | 3 | 70 | 65 | 60 |
| P-18 | 18.7 | | | |
| sethoxydim | 15 | | | |
| imazethapyr | 3 | 50 | 50 | 45 |

TABLE 24-3

| Examples | Dosage g/10a | Herbicidal effect | | |
|---|---|---|---|---|
| | | Edible barn-yard grass | Green fox tail | Shatter-cane |
| sethoxydim | 15 | | | |
| imazethapyr | 3 | 70 | 65 | 60 |
| P-19 | 18.7 | | | |
| sethoxydim | 15 | | | |
| imazethapyr | 3 | 70 | 65 | 60 |
| P-20 | 18.7 | | | |
| sethoxydim | 15 | | | |
| imazethapyr | 3 | 70 | 65 | 60 |
| P-21 | 18.7 | | | |
| sethoxydim | 15 | | | |
| imazethapyr | 3 | 70 | 65 | 60 |
| P-21 | 18.7 | | | |
| sethoxydim | 15 | | | |
| imazethapyr | 3 | 70 | 65 | 60 |
| P-22 | 18.7 | | | |
| sethoxydim | 15 | | | |
| imazethapyr | 3 | 70 | 65 | 60 |
| P-23 | 18.7 | | | |
| sethoxydim | 15 | | | |
| imazethapyr | 3 | 50 | 50 | 45 |

TABLE 24-4

| Examples | Dosage g/10a | Herbicidal effect | | |
|---|---|---|---|---|
| | | Edible barn-yard grass | Green fox tail | Shatter-cane |
| sethoxydim | 15 | | | |
| imazethapyr | 3 | 70 | 65 | 60 |
| P-24 | 18.7 | | | |
| sethoxydim | 15 | | | |
| imazethapyr | 3 | 70 | 65 | 60 |
| P-25 | 18.7 | | | |
| sethoxydim | 15 | | | |
| imazethapyr | 3 | 70 | 65 | 60 |
| P-26 | 18.7 | | | |
| sethoxydim | 15 | | | |
| imazethapyr | 3 | 70 | 65 | 60 |
| P-27 | 18.7 | | | |
| sethoxydim | 15 | | | |
| imazethapyr | 3 | 70 | 65 | 60 |
| P-28 | 18.7 | | | |
| sethoxydim | 15 | | | |
| imazethapyr | 3 | 70 | 65 | 60 |
| P-29 | 18.7 | | | |
| sethoxydim | 15 | | | |

TABLE 24-4-continued

| | Dosage g/10a | Herbicidal effect | | |
|---|---|---|---|---|
| | | Edible barn-yard grass | Green fox tail | Shatter-cane |
| imazethapyr | 3 | 50 | 50 | 45 |

EXAMPLE 15

Herbicidal tests were conductetd in the same manner as in Example 12 except that 25% granular wettable powder of commercially available chlorimuronethyl was used in place of the 40% liquid formulation of bentazon.

Dosages of the herbicides and the antagonism inhibitor per 10a were as follows.

| Sethoxydim | 15 g |
|---|---|
| Chlorimuron-ethyl | 0.8 g |
| Antagonism inhibitor | 18.7 g |

Separately, comparative tests of applying only the mixture of sethoxydim and chlorimuron-ethyl were conducted as comparative control section.

The results are shown in Tables 25-1, 25-2, 25-3 and 25-4.

TABLE 25-1

| | Dosage g/10a | Herbicidal effect | | |
|---|---|---|---|---|
| | | Edible barn-yard grass | Green fox tail | Shatter-cane |
| Examples | | | | |
| sethoxydim | 15 | | | |
| chlorimuron-ethyl | 0.8 | 70 | 65 | 60 |
| P-7 | 18.7 | | | |
| sethoxydim | 15 | | | |
| chlorimuron-ethyl | 0.8 | 70 | 65 | 60 |
| P-8 | 18.7 | | | |
| sethoxydim | 15 | | | |
| chlorimuron-ethyl | 0.8 | 70 | 65 | 60 |
| P-9 | 18.7 | | | |
| sethoxydim | 15 | | | |
| chlorimuron-ethyl | 0.8 | 70 | 65 | 60 |
| P-10 | 18.7 | | | |
| sethoxydim | 15 | | | |
| chlorimuron-ethyl | 0.8 | 70 | 65 | 60 |
| P-11 | 18.7 | | | |
| sethoxydim | 15 | | | |
| chlorimuron-ethyl | 0.8 | 70 | 65 | 60 |
| P-12 | 18.7 | | | |
| sethoxydim | 15 | | | |
| chlorimuron-ethyl | 0.8 | 50 | 50 | 45 |

TABLE 25-2

| | Dosage g/10a | Herbicidal effect | | |
|---|---|---|---|---|
| | | Edible barn-yard grass | Green fox tail | Shatter-cane |
| Examples | | | | |
| sethoxydim | 15 | | | |
| chlorimuron-ethyl | 0.8 | 70 | 65 | 60 |
| P-13 | 18.7 | | | |
| sethoxydim | 15 | | | |
| chlorimuron-ethyl | 0.8 | 70 | 65 | 60 |
| P-14 | 18.7 | | | |
| sethoxydim | 15 | | | |
| chlorimuron-ethyl | 0.8 | 70 | 65 | 60 |
| P-15 | 18.7 | | | |
| sethoxydim | 15 | | | |
| chlorimuron-ethyl | 0.8 | 70 | 65 | 60 |
| P-16 | 18.7 | | | |
| sethoxydim | 15 | | | |
| chlorimuron-ethyl | 0.8 | 70 | 65 | 60 |
| P-17 | 18.7 | | | |

TABLE 25-2-continued

| | Dosage g/10a | Herbicidal effect | | |
|---|---|---|---|---|
| | | Edible barn-yard grass | Green fox tail | Shatter-cane |
| sethoxydim | 15 | | | |
| chlorimuron-ethyl | 0.8 | 70 | 65 | 60 |
| P-18 | 18.7 | | | |
| sethoxydim | 15 | | | |
| chlorimuron-ethyl | 0.8 | 50 | 50 | 45 |

TABLE 25-3

| | Dosage g/10a | Herbicidal effect | | |
|---|---|---|---|---|
| | | Edible barn-yard grass | Green fox tail | Shatter-cane |
| Examples | | | | |
| sethoxydim | 15 | | | |
| chlorimuron-ethyl | 0.8 | 70 | 65 | 60 |
| P-19 | 18.7 | | | |
| sethoxydim | 15 | | | |
| chlorimuron-ethyl | 0.8 | 70 | 65 | 60 |
| P-20 | 18.7 | | | |
| sethoxydim | 15 | | | |
| chlorimuron-ethyl | 0.8 | 70 | 65 | 60 |
| P-21 | 18.7 | | | |
| sethoxydim | 15 | | | |
| chlorimuron-ethyl | 0.8 | 70 | 65 | 60 |
| P-22 | 18.7 | | | |
| sethoxydim | 15 | | | |
| chlorimuron-ethyl | 0.8 | 70 | 65 | 60 |
| P-23 | 18.7 | | | |
| sethoxydim | 15 | | | |
| chlorimuron-ethyl | 0.8 | 50 | 50 | 45 |

TABLE 25-4

| | Dosage g/10a | Herbicidal effect | | |
|---|---|---|---|---|
| | | Edible barn-yard grass | Green fox tail | Shatter-cane |
| Examples | | | | |
| sethoxydim | 15 | | | |
| chlorimuron-ethyl | 0.8 | 70 | 65 | 60 |
| P-24 | 18.7 | | | |
| sethoxydim | 15 | | | |
| chlorimuron-ethyl | 0.8 | 70 | 65 | 60 |
| P-25 | 18.7 | | | |
| sethoxydim | 15 | | | |
| chlorimuron-ethyl | 0.8 | 70 | 65 | 60 |
| P-26 | 18.7 | | | |
| sethoxydim | 15 | | | |
| chlorimuron-ethyl | 0.8 | 70 | 65 | 60 |
| P-27 | 18.7 | | | |
| sethoxydim | 15 | | | |
| chlorimuron-ethyl | 0.8 | 70 | 65 | 60 |
| P-28 | 18.7 | | | |
| sethoxydim | 15 | | | |
| chlorimuron-ethyl | 0.8 | 70 | 65 | 60 |
| P-29 | 18.7 | | | |
| sethoxydim | 15 | | | |
| chlorimuron-ethyl | 0.8 | 50 | 50 | 45 |

EXAMPLE 16

Herbicidal tests were conducted in the same manner as in Example 12 except that 20% liquid formulation of commercially available acifluorfen-sodium was used in place of the 40% liquid formulation of bentazon.

Dosages of the herbicides and the antagonism inhibitor per 10a were as follows.

| Sethoxydim | 15 g |
|---|---|
| Acifluorfen-sodium | 5 g |
| Antagonism inhibitor | 18.7 g |

Separately, comparative tests of applying only the mixture of sethoxydim and acifluorfen-sodium were conducted as comparative control test.

The results are shown in Tables 26-1, 26-2, 26-3 and 26-4.

TABLE 26-1

|  | Dosage g/10a | Herbicidal effect | | |
|---|---|---|---|---|
|  |  | Edible barn-yard grass | Green fox tail | Shatter-cane |
| Examples |  |  |  |  |
| sethoxydim | 15 |  |  |  |
| acifluorfen-sodium | 5 | 85 | 80 | 80 |
| P-7 | 18.7 |  |  |  |
| sethoxydim | 15 |  |  |  |
| acifluorfen-sodium | 5 | 85 | 80 | 80 |
| P-8 | 18.7 |  |  |  |
| sethoxydim | 15 |  |  |  |
| acifluorfen-sodium | 5 | 85 | 80 | 80 |
| P-9 | 18.7 |  |  |  |
| sethoxydim | 15 |  |  |  |
| acifluorfen-sodium | 5 | 85 | 80 | 80 |
| P-10 | 18.7 |  |  |  |
| sethoxydim | 15 |  |  |  |
| acifluorfen-sodium | 5 | 85 | 80 | 80 |
| P-11 | 18.7 |  |  |  |
| sethoxydim | 15 |  |  |  |
| acifluorfen-sodium | 5 | 85 | 80 | 80 |
| P-12 | 18.7 |  |  |  |
| sethoxydim | 15 |  |  |  |
| acifluorfen-sodium | 5 | 55 | 55 | 45 |

TABLE 26-2

|  | Dosage g/10a | Herbicidal effect | | |
|---|---|---|---|---|
|  |  | Edible barn-yard grass | Green fox tail | Shatter-cane |
| Examples |  |  |  |  |
| sethoxydim | 15 |  |  |  |
| acifluorfen-sodium | 5 | 85 | 80 | 80 |
| P-13 | 18.7 |  |  |  |
| sethoxydim | 15 |  |  |  |
| acifluorfen-sodium | 5 | 85 | 80 | 80 |
| P-14 | 18.7 |  |  |  |
| sethoxydim | 15 |  |  |  |
| acifluorfen-sodium | 5 | 85 | 80 | 80 |
| P-15 | 18.7 |  |  |  |
| sethoxydim | 15 |  |  |  |
| acifluorfen-sodium | 5 | 85 | 80 | 80 |
| P-16 | 18.7 |  |  |  |
| sethoxydim | 15 |  |  |  |
| acifluorfen-sodium | 5 | 85 | 80 | 80 |
| P-17 | 18.7 |  |  |  |
| sethoxydim | 15 |  |  |  |
| acifluorfen-sodium | 5 | 85 | 80 | 80 |
| P-18 | 18.7 |  |  |  |
| sethoxydim | 15 |  |  |  |
| acifluorfen-sodium | 5 | 55 | 55 | 45 |

TABLE 26-3

|  | Dosage g/10a | Herbicidal effect | | |
|---|---|---|---|---|
|  |  | Edible barn-yard grass | Green fox tail | Shatter-cane |
| Examples |  |  |  |  |
| sethoxydim | 15 |  |  |  |
| acifluorfen-sodium | 5 | 85 | 80 | 80 |
| P-19 | 18.7 |  |  |  |
| sethoxydim | 15 |  |  |  |
| acifluorfen-sodium | 5 | 85 | 80 | 80 |
| P-20 | 18.7 |  |  |  |
| sethoxydim | 15 |  |  |  |
| acifluorfen-sodium | 5 | 85 | 80 | 80 |
| P-21 | 18.7 |  |  |  |
| sethoxydim | 15 |  |  |  |
| acifluorfen-sodium | 5 | 85 | 80 | 80 |
| P-22 | 18.7 |  |  |  |
| sethoxydim | 15 |  |  |  |

TABLE 26-3-continued

|  | Dosage g/10a | Herbicidal effect | | |
|---|---|---|---|---|
|  |  | Edible barn-yard grass | Green fox tail | Shatter-cane |
| acifluorfen-sodium | 5 | 85 | 80 | 80 |
| P-23 | 18.7 |  |  |  |
| sethoxydim | 15 |  |  |  |
| acifluorfen-sodium | 5 | 55 | 55 | 45 |

TABLE 26-4

|  | Dosage g/10a | Herbicidal effect | | |
|---|---|---|---|---|
|  |  | Edible barn-yard grass | Green fox tail | Shatter-cane |
| Examples |  |  |  |  |
| sethoxydim | 15 |  |  |  |
| acifluorfen-sodium | 5 | 85 | 80 | 80 |
| P-24 | 18.7 |  |  |  |
| sethoxydim | 15 |  |  |  |
| acifluorfen-sodium | 5 | 85 | 80 | 80 |
| P-25 | 18.7 |  |  |  |
| sethoxydim | 15 |  |  |  |
| acifluorfen-sodium | 5 | 85 | 80 | 80 |
| P-26 | 18.7 |  |  |  |
| sethoxydim | 15 |  |  |  |
| acifluorfen-sodium | 5 | 85 | 80 | 80 |
| P-27 | 18.7 |  |  |  |
| sethoxydim | 15 |  |  |  |
| acifluorfen-sodium | 5 | 85 | 80 | 80 |
| P-28 | 18.7 |  |  |  |
| sethoxydim | 15 |  |  |  |
| acifluorfen-sodium | 5 | 85 | 80 | 80 |
| P-29 | 18.7 |  |  |  |
| sethoxydim | 15 |  |  |  |
| acifluorfen-sodium | 5 | 55 | 55 | 45 |

EXAMPLE 17

Herbicidal tests were conducted in the same manner as in Example 12 except that 35% emulsifiable concentrate of commercially available fluazifop-butyl was used in place of the 20% emulsifiable concentrate of sethoxydim.

Dosages of the herbicides and the antagonism inhibitor per 10a were as follows.

| Fluazifop-butyl | 15 g |
|---|---|
| Bentazon | 80 g |
| Antagonism inhibitor | 18.7 g |

Separately, comparative tests of applying only the mixture of fluazifop-butyl and bentazon were conducted as comparative control section.

The results are shown in Tables 27-1, 27-2, 27-3 and 27-4.

TABLE 27-1

|  | Dosage g/10a | Herbicidal effect | | |
|---|---|---|---|---|
|  |  | Edible barn-yard grass | Green fox tail | Shatter-cane |
| Examples |  |  |  |  |
| fluazifop-butyl | 15 |  |  |  |
| bentazon | 80 | 85 | 80 | 80 |
| P-7 | 18.7 |  |  |  |
| fluazifop-butyl | 15 |  |  |  |
| bentazon | 80 | 85 | 80 | 80 |
| P-8 | 18.7 |  |  |  |
| fluazifop-butyl | 15 |  |  |  |
| bentazon | 80 | 85 | 80 | 80 |
| P-9 | 18.7 |  |  |  |
| fluazifop-butyl | 15 |  |  |  |
| bentazon | 80 | 85 | 80 | 80 |
| P-10 | 18.7 |  |  |  |

TABLE 27-1-continued

| | Dosage g/10a | Herbicidal effect | | |
|---|---|---|---|---|
| | | Edible barn-yard grass | Green fox tail | Shatter-cane |
| fluazifop-butyl | 15 | | | |
| bentazon | 80 | 85 | 80 | 80 |
| P-11 | 18.7 | | | |
| fluazifop-butyl | 15 | | | |
| bentazon | 80 | 85 | 80 | 80 |
| P-12 | 18.7 | | | |
| fluazifop-butyl | 15 | | | |
| bentazon | 80 | 55 | 55 | 45 |

TABLE 27-2

| | Dosage g/10a | Herbicidal effect | | |
|---|---|---|---|---|
| | | Edible barn-yard grass | Green fox tail | Shatter-cane |
| Examples | | | | |
| fluazifop-butyl | 15 | | | |
| bentazon | 80 | 85 | 80 | 80 |
| P-13 | 18.7 | | | |
| fluazifop-butyl | 15 | | | |
| bentazon | 80 | 85 | 80 | 80 |
| P-14 | 18.7 | | | |
| fluazifop-butyl | 15 | | | |
| bentazon | 80 | 85 | 80 | 80 |
| P-15 | 18.7 | | | |
| fluazifop-butyl | 15 | | | |
| bentazon | 80 | 85 | 80 | 80 |
| P-16 | 18.7 | | | |
| fluazifop-butyl | 15 | | | |
| bentazon | 80 | 85 | 80 | 80 |
| P-17 | 18.7 | | | |
| fluazifop-butyl | 15 | | | |
| bentazon | 80 | 85 | 80 | 80 |
| P-18 | 18.7 | | | |
| fluazifop-butyl | 15 | | | |
| bentazon | 80 | 55 | 55 | 45 |

TABLE 27-3

| | Dosage g/10a | Herbicidal effect | | |
|---|---|---|---|---|
| | | Edible barn-yard grass | Green fox tail | Shatter-cane |
| Examples | | | | |
| fluazifop-butyl | 15 | | | |
| bentazon | 80 | 85 | 80 | 80 |
| P-19 | 18.7 | | | |
| fluazifop-butyl | 15 | | | |
| bentazon | 80 | 85 | 80 | 80 |
| P-20 | 18.7 | | | |
| fluazifop-butyl | 15 | | | |
| bentazon | 80 | 85 | 80 | 80 |
| P-21 | 18.7 | | | |
| fluazifop-butyl | 15 | | | |
| bentazon | 80 | 85 | 80 | 80 |
| P-22 | 18.7 | | | |
| fluazifop-butyl | 15 | | | |
| bentazon | 80 | 85 | 80 | 80 |
| P-23 | 18.7 | | | |
| fluazifop-butyl | 15 | | | |
| bentazon | 80 | 55 | 55 | 45 |

TABLE 27-4

| | Dosage g/10a | Herbicidal effect | | |
|---|---|---|---|---|
| | | Edible barn-yard grass | Green fox tail | Shatter-cane |
| Examples | | | | |
| fluazifop-butyl | 15 | | | |
| bentazon | 80 | 85 | 80 | 80 |
| P-24 | 18.7 | | | |
| fluazifop-butyl | 15 | | | |
| bentazon | 80 | 85 | 80 | 80 |
| P-25 | 18.7 | | | |
| fluazifop-butyl | 15 | | | |
| bentazon | 80 | 85 | 80 | 80 |
| P-26 | 18.7 | | | |
| fluazifop-butyl | 15 | | | |
| bentazon | 80 | 85 | 80 | 80 |
| P-27 | 18.7 | | | |
| fluazifop-butyl | 15 | | | |
| bentazon | 80 | 85 | 80 | 80 |
| P-28 | 18.7 | | | |
| fluazifop-butyl | 15 | | | |
| bentazon | 80 | 85 | 80 | 80 |
| P-29 | 18.7 | | | |
| fluazifop-butyl | 15 | | | |
| bentazon | 80 | 55 | 55 | 45 |

EXAMPLE 18

Herbicidal tests were conducted in the same manner as in Example 13 except that 35% emulsifiable concentrate of commercially available fluazifop-butyl was used in place of the 20% emulsifiable concentrate of sethoxydim.

Dosages of the herbicides and the antagonism inhibitor per 10a were as follows.

| Fluazifop-butyl | 15 g |
|---|---|
| Imazaquin | 10 g |
| Antagonism inhibitor | 18.7 g |

Separately, comparative tests of applying only the mixture of fluazifop-butyl and imazaqion were conducted as comparative control section.

The results are shown in Tables 28-1, 28-2, 8-3 and 28-4.

TABLE 28-1

| | Dosage g/10a | Herbicidal effect | | |
|---|---|---|---|---|
| | | Edible barn-yard grass | Green fox tail | Shatter-cane |
| Examples | | | | |
| fluazifop-butyl | 15 | | | |
| imazaquin | 10 | 70 | 65 | 60 |
| P-7 | 18.7 | | | |
| fluazifop-butyl | 15 | | | |
| imazaquin | 10 | 70 | 65 | 60 |
| P-8 | 18.7 | | | |
| fluazifop-butyl | 15 | | | |
| imazaquin | 10 | 70 | 65 | 60 |
| P-9 | 18.7 | | | |
| fluazifop-butyl | 15 | | | |
| imazaquin | 10 | 70 | 65 | 60 |
| P-10 | 18.7 | | | |
| fluazifop-butyl | 15 | | | |
| imazaquin | 10 | 70 | 65 | 60 |
| P-11 | 18.7 | | | |
| fluazifop-butyl | 15 | | | |
| imazaquin | 10 | 70 | 65 | 60 |
| P-12 | 18.7 | | | |
| fluazifop-butyl | 15 | | | |
| imazaquin | 10 | 50 | 50 | 45 |

TABLE 28-2

| | Dosage g/10a | Herbicidal effect | | |
|---|---|---|---|---|
| | | Edible barn-yard grass | Green fox tail | Shatter-cane |
| Examples | | | | |
| fluazifop-butyl | 15 | | | |
| imazaquin | 10 | 70 | 65 | 60 |

TABLE 28-2-continued

|  | Dosage g/10a | Herbicidal effect | | |
|---|---|---|---|---|
|  |  | Edible barn-yard grass | Green fox tail | Shatter-cane |
| P-13 | 18.7 | | | |
| fluazifop-butyl | 15 | | | |
| imazaquin | 10 | 70 | 65 | 60 |
| P-14 | 18.7 | | | |
| fluazifop-butyl | 15 | | | |
| imazaquin | 10 | 70 | 65 | 60 |
| P-15 | 18.7 | | | |
| fluazifop-butyl | 15 | | | |
| imazaquin | 10 | 70 | 65 | 60 |
| P-16 | 18.7 | | | |
| fluazifop-butyl | 15 | | | |
| imazaquin | 10 | 70 | 65 | 60 |
| P-17 | 18.7 | | | |
| fluazifop-butyl | 15 | | | |
| imazaquin | 10 | 70 | 65 | 60 |
| P-18 | 18.7 | | | |
| fluazifop-butyl | 15 | | | |
| imazaquin | 10 | 50 | 50 | 45 |

TABLE 28-3

|  | Dosage g/10a | Herbicidal effect | | |
|---|---|---|---|---|
|  |  | Edible barn-yard grass | Green fox tail | Shatter-cane |
| Examples |  |  |  |  |
| fluazifop-butyl | 15 | | | |
| imazaquin | 10 | 70 | 65 | 60 |
| P-19 | 18.7 | | | |
| fluazifop-butyl | 15 | | | |
| imazaquin | 10 | 70 | 65 | 60 |
| P-20 | 18.7 | | | |
| fluazifop-butyl | 15 | | | |
| imazaquin | 10 | 70 | 65 | 60 |
| P-21 | 18.7 | | | |
| fluazifop-butyl | 15 | | | |
| imazaquin | 10 | 70 | 65 | 60 |
| P-22 | 18.7 | | | |
| fluazifop-butyl | 15 | | | |
| imazaquin | 10 | 70 | 65 | 60 |
| P-23 | 18.7 | | | |
| fluazifop-butyl | 15 | | | |
| imazaquin | 10 | 50 | 50 | 45 |

TABLE 28-4

|  | Dosage g/10a | Herbicidal effect | | |
|---|---|---|---|---|
|  |  | Edible barn-yard grass | Green fox tail | Shatter-cane |
| Examples |  |  |  |  |
| fluazifop-butyl | 15 | | | |
| imazaquin | 10 | 70 | 65 | 60 |
| P-24 | 18.7 | | | |
| fluazifop-butyl | 15 | | | |
| imazaquin | 10 | 70 | 65 | 60 |
| P-25 | 18.7 | | | |
| fluazifop-butyl | 15 | | | |
| imazaquin | 10 | 70 | 65 | 60 |
| P-26 | 18.7 | | | |
| fluazifop-butyl | 15 | | | |
| imazaquin | 10 | 70 | 65 | 60 |
| P-27 | 18.7 | | | |
| fluazifop-butyl | 15 | | | |
| imazaquin | 10 | 70 | 65 | 60 |
| P-28 | 18.7 | | | |
| fluazifop-butyl | 15 | | | |
| imazaquin | 10 | 70 | 65 | 60 |
| P-29 | 18.7 | | | |
| fluazifop-butyl | 15 | | | |
| imazaquin | 10 | 50 | 50 | 45 |

EXAMPLE 19

Herbicidal tests were conducted in the same manner as in Example 14 except that 35% emulsifiable concentrate of commercially available fluazifop-butyl was used in place of the 20% emulsifiable concentrate of sethoxydim.

Dosages of the herbicides and the antagonism inhibitor per 10a were as follows.

| Fluazifop-butyl | 15 g |
| Imazethapyr | 3 g |
| Antagonism inhibitor | 18.7 g |

Separately, comparative tests of applying only the mixture of fluazifop-butyl and imazethapyr were conducted as comparative control section.

The results are shown in Tables 29-1, 29-2, 29-3 and 29-4.

TABLE 29-1

|  | Dosage g/10a | Herbicidal effect | | |
|---|---|---|---|---|
|  |  | Edible barn-yard grass | Green fox tail | Shatter-cane |
| Examples |  |  |  |  |
| fluazifop-butyl | 15 | | | |
| imazethapyr | 3 | 70 | 65 | 60 |
| P-7 | 18.7 | | | |
| fluazifop-butyl | 15 | | | |
| imazethapyr | 3 | 70 | 65 | 60 |
| P-8 | 18.7 | | | |
| fluazifop-butyl | 15 | | | |
| imazethapyr | 3 | 70 | 65 | 60 |
| P-9 | 18.7 | | | |
| fluazifop-butyl | 15 | | | |
| imazethapyr | 3 | 70 | 65 | 60 |
| P-10 | 18.7 | | | |
| fluazifop-butyl | 15 | | | |
| imazethapyr | 3 | 70 | 65 | 60 |
| P-11 | 18.7 | | | |
| fluazifop-butyl | 15 | | | |
| imazethapyr | 3 | 70 | 65 | 60 |
| P-12 | 18.7 | | | |
| fluazifop-butyl | 15 | | | |
| imazethapyr | 3 | 50 | 50 | 45 |

TABLE 29-2

|  | Dosage g/10a | Herbicidal effect | | |
|---|---|---|---|---|
|  |  | Edible barn-yard grass | Green fox tail | Shatter-cane |
| Examples |  |  |  |  |
| fluazifop-butyl | 15 | | | |
| imazethapyr | 3 | 70 | 65 | 60 |
| P-13 | 18.7 | | | |
| fluazifop-butyl | 15 | | | |
| imazethapyr | 3 | 70 | 65 | 60 |
| P-14 | 18.7 | | | |
| fluazifop-butyl | 15 | | | |
| imazethapyr | 3 | 70 | 65 | 60 |
| P-15 | 18.7 | | | |
| fluazifop-butyl | 15 | | | |
| imazethapyr | 3 | 70 | 65 | 60 |
| P-16 | 18.7 | | | |
| fluazifop-butyl | 15 | | | |
| imazethapyr | 3 | 70 | 65 | 60 |
| P-17 | 18.7 | | | |
| fluazifop-butyl | 15 | | | |
| imazethapyr | 3 | 70 | 65 | 60 |
| P-18 | 18.7 | | | |
| fluazifop-butyl | 15 | | | |
| imazethapyr | 3 | 50 | 50 | 45 |

TABLE 29-3

| Examples | Dosage g/10a | Herbicidal effect | | |
|---|---|---|---|---|
| | | Edible barn-yard grass | Green fox tail | Shatter-cane |
| fluazifop-butyl | 15 | | | |
| imazethapyr | 3 | 70 | 65 | 60 |
| P-19 | 18.7 | | | |
| fluazifop-butyl | 15 | | | |
| imazethapyr | 3 | 70 | 65 | 60 |
| P-20 | 18.7 | | | |
| fluazifop-butyl | 15 | | | |
| imazethapyr | 3 | 70 | 65 | 60 |
| P-21 | 18.7 | | | |
| fluazifop-butyl | 15 | | | |
| imazethapyr | 3 | 70 | 65 | 60 |
| P-22 | 18.7 | | | |
| fluazifop-butyl | 15 | | | |
| imazethapyr | 3 | 70 | 65 | 60 |
| P-23 | 18.7 | | | |
| fluazifop-butyl | 15 | | | |
| imazethapyr | 3 | 50 | 50 | 45 |

TABLE 29-4

| Examples | Dosage g/10a | Herbicidal effect | | |
|---|---|---|---|---|
| | | Edible barn-yard grass | Green fox tail | Shatter-cane |
| fluazifop-butyl | 15 | | | |
| imazethapyr | 3 | 70 | 65 | 60 |
| P-24 | 18.7 | | | |
| fluazifop-butyl | 15 | | | |
| imazethapyr | 3 | 70 | 65 | 60 |
| P-25 | 18.7 | | | |
| fluazifop-butyl | 15 | | | |
| imazethapyr | 3 | 70 | 65 | 60 |
| P-26 | 18.7 | | | |
| fluazifop-butyl | 15 | | | |
| imazethapyr | 3 | 70 | 65 | 60 |
| P-27 | 18.7 | | | |
| fluazifop-butyl | 15 | | | |
| imazethapyr | 3 | 70 | 65 | 60 |
| P-28 | 18.7 | | | |
| fluazifop-butyl | 15 | | | |
| imazethapyr | 3 | 70 | 65 | 60 |
| P-29 | 18.7 | | | |
| fluazifop-butyl | 15 | | | |
| imazethapyr | 3 | 50 | 50 | 45 |

EXAMPLE 20

Herbicidal tests were conducted in the same manner as in Example 15 except that 35% emulsifiable concentrate of commercially available fluazifop-butyl was used in place of the 20% emulsifiable concentrate of sethoxydim.

Dosages of the herbicides and the antagonism inhibitor per 10a were as follows.

| Fluazifop-butyl | 15 g |
|---|---|
| Chlorimuron-ethyl | 0.8 g |
| Antagonism inhibitor | 18.7 g |

Separately, comparative tests of applying only the mixture of fluazifop-butyl and chlorimuronethyl were conducted as comparative control section.

The results are shown in Tables 30-1, 30-2, 30-3 and 30-4.

TABLE 30-1

| Examples | Dosage g/10a | Herbicidal effect | | |
|---|---|---|---|---|
| | | Edible barn-yard grass | Green fox tail | Shatter-cane |
| fluazifop-butyl | 15 | | | |
| chlorimuron-ethyl | 0.8 | 70 | 65 | 60 |
| P-7 | 18.7 | | | |
| fluazifop-butyl | 15 | | | |
| chlorimuron-ethyl | 0.8 | 70 | 65 | 60 |
| P-8 | 18.7 | | | |
| fluazifop-butyl | 15 | | | |
| chlorimuron-ethyl | 0.8 | 70 | 65 | 60 |
| P-9 | 18.7 | | | |
| fluazifop-butyl | 15 | | | |
| chlorimuron-ethyl | 0.8 | 70 | 65 | 60 |
| P-10 | 18.7 | | | |
| fluazifop-butyl | 15 | | | |
| chlorimuron-ethyl | 0.8 | 70 | 65 | 60 |
| P-11 | 18.7 | | | |
| fluazifop-butyl | 15 | | | |
| chlorimuron-ethyl | 0.8 | 70 | 65 | 60 |
| P-12 | 18.7 | | | |
| fluazifop-butyl | 15 | | | |
| chlorimuron-ethyl | 0.8 | 50 | 50 | 45 |

TABLE 30-2

| Examples | Dosage g/10a | Herbicidal effect | | |
|---|---|---|---|---|
| | | Edible barn-yard grass | Green fox tail | Shatter-cane |
| fluazifop-butyl | 15 | | | |
| chlorimuron-ethyl | 0.8 | 70 | 65 | 60 |
| P-13 | 18.7 | | | |
| fluazifop-butyl | 15 | | | |
| chlorimuron-ethyl | 0.8 | 70 | 65 | 60 |
| P-14 | 18.7 | | | |
| fluazifop-butyl | 15 | | | |
| chlorimuron-ethyl | 0.8 | 70 | 65 | 60 |
| P-15 | 18.7 | | | |
| fluazifop-butyl | 15 | | | |
| chlorimuron-ethyl | 0.8 | 70 | 65 | 60 |
| P-16 | 18.7 | | | |
| fluazifop-butyl | 15 | | | |
| chlorimuron-ethyl | 0.8 | 70 | 65 | 60 |
| P-17 | 18.7 | | | |
| fluazifop-butyl | 15 | | | |
| chlorimuron-ethyl | 0.8 | 70 | 65 | 60 |
| P-18 | 18.7 | | | |
| fluazifop-butyl | 15 | | | |
| chlorimuron-ethyl | 0.8 | 50 | 50 | 45 |

TABLE 30-3

| Examples | Dosage g/10a | Herbicidal effect | | |
|---|---|---|---|---|
| | | Edible barn-yard grass | Green fox tail | Shatter-cane |
| fluazifop-butyl | 15 | | | |
| chlorimuron-ethyl | 0.8 | 70 | 65 | 60 |
| P-19 | 18.7 | | | |
| fluazifop-butyl | 15 | | | |
| chlorimuron-ethyl | 0.8 | 70 | 65 | 60 |
| P-20 | 18.7 | | | |
| fluazifop-butyl | 15 | | | |
| chlorimuron-ethyl | 0.8 | 70 | 65 | 60 |
| P-21 | 18.7 | | | |
| fluazifop-butyl | 15 | | | |
| chlorimuron-ethyl | 0.8 | 70 | 65 | 60 |
| P-22 | 18.7 | | | |
| fluazifop-butyl | 15 | | | |
| chlorimuron-ethyl | 0.8 | 70 | 65 | 60 |
| P-23 | 18.7 | | | |
| fluazifop-butyl | 15 | | | |
| chlorimuron-ethyl | 0.8 | 50 | 50 | 45 |

TABLE 30-4

| Examples | Dosage g/10a | Herbicidal effect | | |
|---|---|---|---|---|
| | | Edible barnyard grass | Green fox tail | Shattercane |
| fluazifop-butyl<br>chlorimuron-ethyl<br>P-24 | 15<br>0.8<br>18.7 | 70 | 65 | 60 |
| fluazifop-butyl<br>chlorimuron-ethyl<br>P-25 | 15<br>0.8<br>18.7 | 70 | 65 | 60 |
| fluazifop-butyl<br>chlorimuron-ethyl<br>P-26 | 15<br>0.8<br>18.7 | 70 | 65 | 60 |
| fluazifop-butyl<br>chlorimuron-ethyl<br>P-27 | 15<br>0.8<br>18.7 | 70 | 65 | 60 |
| fluazifop-butyl<br>chlorimuron-ethyl<br>P-28 | 15<br>0.8<br>18.7 | 70 | 65 | 60 |
| fluazifop-butyl<br>chlorimuron-ethyl<br>P-29 | 15<br>0.8<br>18.7 | 70 | 65 | 60 |
| fluazifop-butyl<br>chlorimuron-ethyl | 15<br>0.8 | 50 | 50 | 45 |

EXAMPLE 21

Herbicidal tests were conducted in the same manner as in Example 16 except that 35% emulsifiable concentrate of commercially available fluazifop-butyl was used in place of the 20% emulsifiable concentrate of sethoxydim.

Dosages of the herbicides and the antagonism inhibitor per 10a were as follows.

| | |
|---|---|
| Fluazifop-butyl | 15 g |
| Acifluorfen-sodium | 5 g |
| Antagonism inhibitor | 18.7 g |

Separately, comparative tests of applying only the mixture of fluazifop-butyl and acifluorfen-sodium were conducted as comparative control section.

The results are shown in Tables 31-1, 31-2, 1-3 and 31-4.

TABLE 31-1

| Examples | Dosage g/10a | Herbicidal effect | | |
|---|---|---|---|---|
| | | Edible barnyard grass | Green fox tail | Shattercane |
| fluazifop-butyl<br>acifluorfen-sodium<br>P-7 | 15<br>5<br>18.7 | 85 | 80 | 80 |
| fluazifop-butyl<br>acifluorfen-sodium<br>P-8 | 15<br>5<br>18.7 | 85 | 80 | 80 |
| fluazifop-butyl<br>acifluorfen-sodium<br>P-9 | 15<br>5<br>18.7 | 85 | 80 | 80 |
| fluazifop-butyl<br>acifluorfen-sodium<br>P-10 | 15<br>5<br>18.7 | 85 | 80 | 80 |
| fluazifop-butyl<br>acifluorfen-sodium<br>P-11 | 15<br>5<br>18.7 | 85 | 80 | 80 |
| fluazifop-butyl<br>acifluorfen-sodium<br>P-12 | 15<br>5<br>18.7 | 85 | 80 | 80 |
| fluazifop-butyl<br>acifluorfen-sodium | 15<br>5 | 55 | 55 | 45 |

TABLE 31-2

| Examples | Dosage g/10a | Herbicidal effect | | |
|---|---|---|---|---|
| | | Edible barnyard grass | Green fox tail | Shattercane |
| fluazifop-butyl<br>acifluorfen-sodium<br>P-13 | 15<br>5<br>18.7 | 85 | 80 | 80 |
| fluazifop-butyl<br>acifluorfen-sodium<br>P-14 | 15<br>5<br>18.7 | 85 | 80 | 80 |
| fluazifop-butyl<br>acifluorfen-sodium<br>P-15 | 15<br>5<br>18.7 | 85 | 80 | 80 |
| fluazifop-butyl<br>acifluorfen-sodium<br>P-16 | 15<br>5<br>18.7 | 85 | 80 | 80 |
| fluazifop-butyl<br>acifluorfen-sodium<br>P-17 | 15<br>5<br>18.7 | 85 | 80 | 80 |
| fluazifop-butyl<br>acifluorfen-sodium<br>P-18 | 15<br>5<br>18.7 | 85 | 80 | 80 |
| fluazifop-butyl<br>acifluorfen-sodium | 15<br>5 | 55 | 55 | 45 |

TABLE 31-3

| Examples | Dosage g/10a | Herbicidal effect | | |
|---|---|---|---|---|
| | | Edible barnyard grass | Green fox tail | Shattercane |
| fluazifop-butyl<br>acifluorfen-sodium<br>P-19 | 15<br>5<br>18.7 | 85 | 80 | 80 |
| fluazifop-butyl<br>acifluorfen-sodium<br>P-20 | 15<br>5<br>18.7 | 85 | 80 | 80 |
| fluazifop-butyl<br>acifluorfen-sodium<br>P-21 | 15<br>5<br>18.7 | 85 | 80 | 80 |
| fluazifop-butyl<br>acifluorfen-sodium<br>P-22 | 15<br>5<br>18.7 | 85 | 80 | 80 |
| fluazifop-butyl<br>acifluorfen-sodium<br>P-23 | 15<br>5<br>18.7 | 85 | 80 | 80 |
| fluazifop-butyl<br>acifluorfen-sodium | 15<br>5 | 55 | 55 | 45 |

TABLE 31-4

| Examples | Dosage g/10a | Herbicidal effect | | |
|---|---|---|---|---|
| | | Edible barnyard grass | Green fox tail | Shattercane |
| fluazifop-butyl<br>acifluorfen-sodium<br>P-24 | 15<br>5<br>18.7 | 85 | 80 | 80 |
| fluazifop-butyl<br>acifluorfen-sodium<br>P-25 | 15<br>5<br>18.7 | 85 | 80 | 80 |
| fluazifop-butyl<br>acifluorfen-sodium<br>P-26 | 15<br>5<br>18.7 | 85 | 80 | 80 |
| fluazifop-butyl<br>acifluorfen-sodium<br>P-27 | 15<br>5<br>18.7 | 85 | 80 | 80 |
| fluazifop-butyl<br>acifluorfen-sodium<br>P-28 | 15<br>5<br>18.7 | 85 | 80 | 80 |
| fluazifop-butyl<br>acifluorfen-sodium<br>P-29 | 15<br>5<br>18.7 | 85 | 80 | 80 |
| fluazifop-butyl<br>acifluorfen-sodium | 15<br>5 | 50 | 50 | 45 |

EXAMPLE 22

Field tests were conducted in the State of Missouri and Louisiana, United States of Americla.

A 20% emulsifiable concentrate of commercially available sethoxydim was diluted with water so as to give a dosage of sethoxydim of 30 g/10a. Furthermore, a 40% liqud formulation of commercially available bentazon was diluted with water so as to give a dosage of bentazon of 80 g/10a. Those diluted liquids were mixed, and to the mixture was added the quaternary ammonium salt-containing polymeric compound as the antagonism inhibitor at a concentration of 0.2% by weight on the basis of the amount of the liquid to be applied. On the other hand, to the mixture were added the quaternary ammonium salt-containing polymeric compound as the antagonism inhibitor at a concentration of 0.2% by weight, and a mineral oil at a concentration of 1% by weight, both being on the basis of the amount of the liquid to be applied.

Each of the resulting compositions was applied (sprayed) at a rate of 18.7 liters/10a.

These application amounts correspond to dosages of 15 g, 80 g, 37.4 g and 187 ml of sethoxydim, bentazon, the antagonism inhibitor and the mineral oil, respectively.

Furthermore, a comparative test of applying on the mixutre of sethoxydim and bentazon was conducted.

Test plants and their growing stages when the compositions were applied were as follows.

| | |
|---|---|
| *Setaria faberii* | 7–9 leaf stage |
| *Bracharia platyphylla* | 7–9 leaf stage |
| *Sorghum halepense* | 7–9 leaf stage |
| *Sorghum bicolor* | 7–9 leaf stage |
| *Glycine max* | 7th compound leaf stage |

The application method was spraying.

The herbicidal effects were visually evaluated on 20th day after the application. Complete kill of the weeds was graded to be 100, while no kill of the weeds (no application of the herbicides) was graded to be 0.

The results are shown in Table 32-1.

EXAMPLE 23

Field tests were conducted in the States of Missouri and Louisiana, United States of America.

A 20% emulsifiable concentrate of commercially available sethoxydim was diluted with water so as to give a dosage of sethoxydim of 30 g/10a. Furthermore, a 20% liquid formulation of commercially available imazethapyr was diluted with water so as to give a dosage of imazethapyr of 7 g/10a. These diluted liquids were mixed, and to the mixture was added the quaternary ammonium salt-containing polymeric compound as the antagonism inhibitor at a concentration of 0.03% by weight on the basis of the amount of the liquid to be applied. On the other hand, to the mixture were added the quaternary ammonium salt-containing polymeric compound as the antagonism inhibitor at a concentration of 0.03% by weight, and a mineral oil at a concentration of 1% by weight, both being on the basis of the amount of the liquid to be applied.

Each of the resulting compositions was applied (sprayed) at a rate of 18.7 liters/10a.

These application amounts corresponds to dosages of 15 g, 80 g, 5.61 g and 187 ml of sethoxydim, imazethapyr, the antagonism inhibitor and the mineral oil, respectively.

Furthermore, comparative tests of applying on the mixture of sethoxydim and imazethapyr were conducted.

Test plants and their growing stages when the compositons were applied were as follows.

| | |
|---|---|
| *Setaria faberii* | 4–5 leaf stage |
| *Brachiaria ramosa* | 4–5 leaf stage |
| *Leptochloa dubia* | 4–5 leaf stage |
| *Panicum antidotale* | 4–5 leaf stage |
| *Glycine max* | 2th compound leaf stage |

The application method was spraying.

The herbicidal effects were visually evaluated on 20th day after the application. Complete kill of the weeds was graded to be 100, while no kill of the weeds (no application of the herbicides) was graded to be 0.

The results are shown in Table 32-2.

TABLE 32-1

| Compounds | Dosage (g a.i./a) | Herbicidal effect | | | | Chemical injury |
|---|---|---|---|---|---|---|
| | | SETFA | BRAPP | SORHA | SORVU | GLXMA |
| Examples | | | | | | |
| NP + BAS + P-1 | 3 + 8 + 3.74 | 60 | 60 | 57 | 57 | 0 |
| NP + BAS + P-1 + PO-1 | 3 + 8 + 3.74 + (18.7 ml) | 63 | 67 | 70 | 67 | 0 |
| Comparative test | | | | | | |
| NP + BAS | 3 + 8 | 47 | 43 | 47 | 43 | 0 |

NP: sethoxydim
BAS: bentazon
PO-1: Machine oil base

TABLE 32-2

| Compounds | Dosage (g a.i./a) | Herbicidal effect | | | | Chemical injury |
|---|---|---|---|---|---|---|
| | | SETFA | PANRA | LEFDU | PANAN | GLXMA |
| Examples | | | | | | |
| NP + AC + P-1 | 3 + 0.7 + 0.561 | 90 | 50 | 35 | 72 | 0 |
| NP + AC + P-1 + PO-1 | 3 + 0.7 + 0.561 + (18.7ml) | 93 | 58 | 35 | 85 | 0 |
| Comparative test | | | | | | |

TABLE 32-2-continued

| Compounds | Dosage (g a.i./a) | Herbicidal effect | | | | Chemical injury |
| --- | --- | --- | --- | --- | --- | --- |
| | | SETFA | PANRA | LEFDU | PANAN | GLXMA |
| NP + AC | 3 + 0.7 | 67 | 20 | 18 | 60 | 0 |

NP: sethoxydim
AC: imazethapyr
PO-1: Machine oil base
SETFA = Setaria faberii
PANRA = Brachiaria ramosa
BRAPP = Brachiaria platyphylla
LEFDU = Leptochloa dubia
SORHA = Sorghum halepense
PANAN = Panicum antidotale
SORVU = Sorghum bicolor
GLXMA = Glycine max The antagonism caused by using a herbicide for narrowleaf weeds and a herbicide for broadleaf weeds in combination can be prevented by carrying out weeding using a herbicide composition comprising these herbicides and the antagonsim inhibitor of the present invention. Since the weeding can be performed with less labor and without increasing the amounts of auxilary agents, carriers and herbicides, the possibility of occurrence of chemical injury can be diminished and efficient weeding is possible and besides, environmental contamination can also be reduced. Thus, the present invention makes a great contribution to the industries. The effect of the antagonism inhibitor of the present invention can further be enhanced by using adjuvants in combination.

What is claimed is:

1. A herbicidal composition which is a combination of a herbicide for narrowleaf weeds selected from the group consisting of sethoxydim, fluazifop and quizalofop together with a herbicide for broadleaf weeds selected from the group consisting of bentazon, imazaquin, aciflourfen, fomesafen, chlorimuron, imazethapyr and thifensulfuron, said combination being mixed with an amount of a hydrophillic quaternary ammonium salt which is effective to inhibit the antagonism normally associated with such combination, said quaternary ammonium salt having a molecular weight of from about 10,000 to 1,000,000 and being represented by the formula:

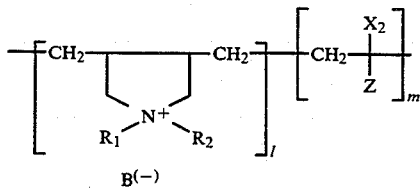

wherein B represents Cl or Br, X₂ represents a hydrogen atom or methyl, each of R₁ and R₂ represents a methyl, ethyl or propyl group with the total carbon number of R₁+R₂ is 2 to 6;
Z represents

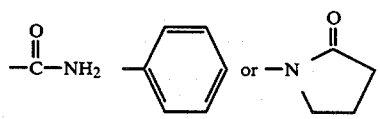

and the ratio of l:m is 5:95 to 100:1.

2. The composition of claim 1 in which the ratio of broadleaf herbicide to narrowleaf herbicide is from 50:1 to 1:5000.

3. The composition of claim 1 additionally containing from 0.01 to 3% of an agriculturally acceptable adjuvant.

4. A method which comprises applying to undesirable herbs a herbicidally effective amount of a composition which is combination of a herbicide for narrowleaf weeds selected from the group consisting of sethoxydim, fluazifop and quizalofop together with a herbicide for broadleaf weeds selected from the group consisting of bentazon, imazaquin, aciflourfen, fomesafen, chlorimuron, imazethapyr and thifensulfuron, said combination being mixed with an amount of a hydrophilic quartternary ammonium salt which is effective to inhibit the antagonism normally associated with such combination, said quanternary ammonium salt having a molecular weight of from about 10,000 to 1,000,000 and being represented by the formula:

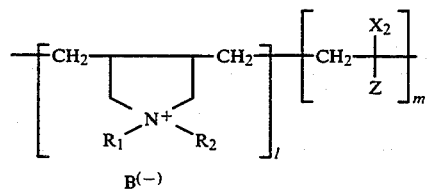

wherein B represents Cl or Br, X₂ represents a hydrogen atom or methyl, each of R₁ and R₂ represents a methyl, ethyl or propyl group with the total carbon number of R₁+R₂ is 2 to 6;
Z represents

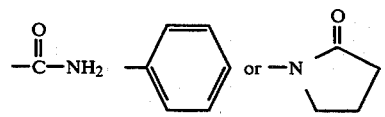

and the ratio of l:m is 5:95 to 100:1.

5. The method of claim 4 in which the ratio of broadleaf herbicide to narrowleaf herbicide in the herbicidal composition is from 50:1 to 1:5000.

6. The method of claim 4 in which the herbicidal composition additionally contains from 0.01 to 3% of an agriculturally acceptable adjuvant.

* * * * *